US008466605B2

(12) United States Patent
Kushculey et al.

(10) Patent No.: US 8,466,605 B2
(45) Date of Patent: Jun. 18, 2013

(54) PATTERNED ULTRASONIC TRANSDUCERS

(75) Inventors: Leonid Kushculey, Rebovot (IL); Vladimir Goland, Ashdod (IL)

(73) Assignee: UltraShape Ltd., Yokneam (IL)

(*) Notice: Subject to any disclaimer, the term of this patent is extended or adjusted under 35 U.S.C. 154(b) by 873 days.

(21) Appl. No.: 12/081,378

(22) Filed: Apr. 15, 2008

(65) Prior Publication Data

US 2009/0230822 A1 Sep. 17, 2009

Related U.S. Application Data

(60) Provisional application No. 61/064,582, filed on Mar. 13, 2008.

(51) Int. Cl.
*H01L 41/00* (2006.01)
(52) U.S. Cl.
USPC .......................................... 310/334; 310/366
(58) Field of Classification Search
USPC ............................................ 310/344, 366, 334
See application file for complete search history.

(56) References Cited

U.S. PATENT DOCUMENTS

| | | | | |
|---|---|---|---|---|
| 2,863,076 | A * | 12/1958 | Koren | 310/359 |
| 3,569,963 | A * | 3/1971 | Mallory et al. | 340/384.7 |
| 5,546,946 | A * | 8/1996 | Souquet | 600/459 |
| 6,563,930 | B1 * | 5/2003 | Nakamura et al. | 381/190 |
| 6,607,498 | B2 * | 8/2003 | Eshel | 601/2 |
| 6,820,313 | B2 * | 11/2004 | Gauchet | 29/25.35 |
| 7,273,459 | B2 | 9/2007 | Desilets et al. | |
| 2003/0229331 | A1 * | 12/2003 | Brisken et al. | 604/500 |
| 2006/0100522 | A1 * | 5/2006 | Yuan et al. | 600/466 |
| 2006/0273696 | A1 * | 12/2006 | Toda | 310/348 |
| 2007/0222339 | A1 * | 9/2007 | Lukacs et al. | 310/335 |
| 2008/0015435 | A1 * | 1/2008 | Cribbs et al. | 600/437 |

OTHER PUBLICATIONS

U.S. Appl. No. 12/003,811, filed Jan. 2, 2008, Kushculey, et al.
Shaw, et al, "Requirements for Measurement Sstandards in High Intensity Focused Ultrasound (HIFU) Fields", NPL Report DQL AC 015, National Physical Laboratory, Middlesex, UK, Feb. 2006.
Hampfrey, V.F., "Ultrasound and Matter—Physical Interactions", Progress in Biophysics and Molecular Biology, 93, pp. 195-211, 2007.
Pennes, H.H., "Analysis of tissue and arterial blood temperatures in the resting human forearm", J. Appl. Physiol. 1, Pp. 93-122, 1948.
Goland, et al., "Strongly Curved Short Focus Annular Array for Therapeutic Applications", Proceedings of the 2006 IEEE Ultrasonics Symposium, pp. 2345-2348, Vancouver, 2006.
Burov, et al, "Nonlinear Ultrasound: Breakdown of Microscopic Biological Structures and Nonthermal Impact on a Malignant Tumor", Doclady Biochemistry and Biophysics, 383, pp. 101-104, 2002.
Wells, P.N.T., "Ultrasonic Imaging of the Body", Rep. Prog. Phys. 62, pp. 671-722, 1999.

(Continued)

*Primary Examiner* — Thomas Dougherty
*Assistant Examiner* — Bryan Gordon
(74) *Attorney, Agent, or Firm* — Manelli Selter PLLC; Edward J. Stemberger

(57) ABSTRACT

There is provided a transducer array for lysing an adipose tissue, the transducer array comprising at least one unitary piece of piezoelectric material having first and second opposing surfaces; and one or more conductive layers on each of said first and second opposing surfaces, wherein at least one of said one or more conductive layers comprises a plurality of electrode elements.

2 Claims, 15 Drawing Sheets

OTHER PUBLICATIONS

Ter Haar, G., "Therapeutic Applications of Ultrasound", Progress in Biophysics and Molecular Biology, 93, pp. 111-129, 2007.

Xu, Zhen, et al, "Controlled ultrasound tissue erosion: The role of dynamic interaction between insonation and microbubble activity", J. Acoust. Soc. Am. 117, (1), pp. 424-435, 2005.

Parsons, et al, "Pulsed cavitational ultrasound therapy for controlled tissue homogenization", Ultrasound in Med. & Biology, 32, pp. 115-126, 2006.

Coleman, et al, "The Cavitation Threshold of Human Tissue Exposed to 0.2 MHz Pulsed Ultrasound: Preliminary Measurements Based on a Study of Clinical Lithotripsy", Ultrasound in Med. & Biol., 21, pp. 405-417, 1995.

Xu, Zhen, et al, "Size measurement of tissue debris generated from mechanical tissue fractionation by cavitational pulsed ultrasound therapy—histotripsy", $6^{th}$ International Symposium on Therapeutic Ultrasound, 2006.

Teitelbaum, et al, "Noninvasive Body Contouring by Focused Ultrasound: Safety and Efficacy of the UltraShape Device in a Multicenter, Controlled Clinical Study", Plastic and Reconstruction Survery, 120, pp. 779-789, 2007.

Moreno, et al, "Body Contouring by Non-Invasive Transdermal Focused Ultrasound", Lasers in Surgery and Medicine, 39, pp. 315-323, 2007.

* cited by examiner

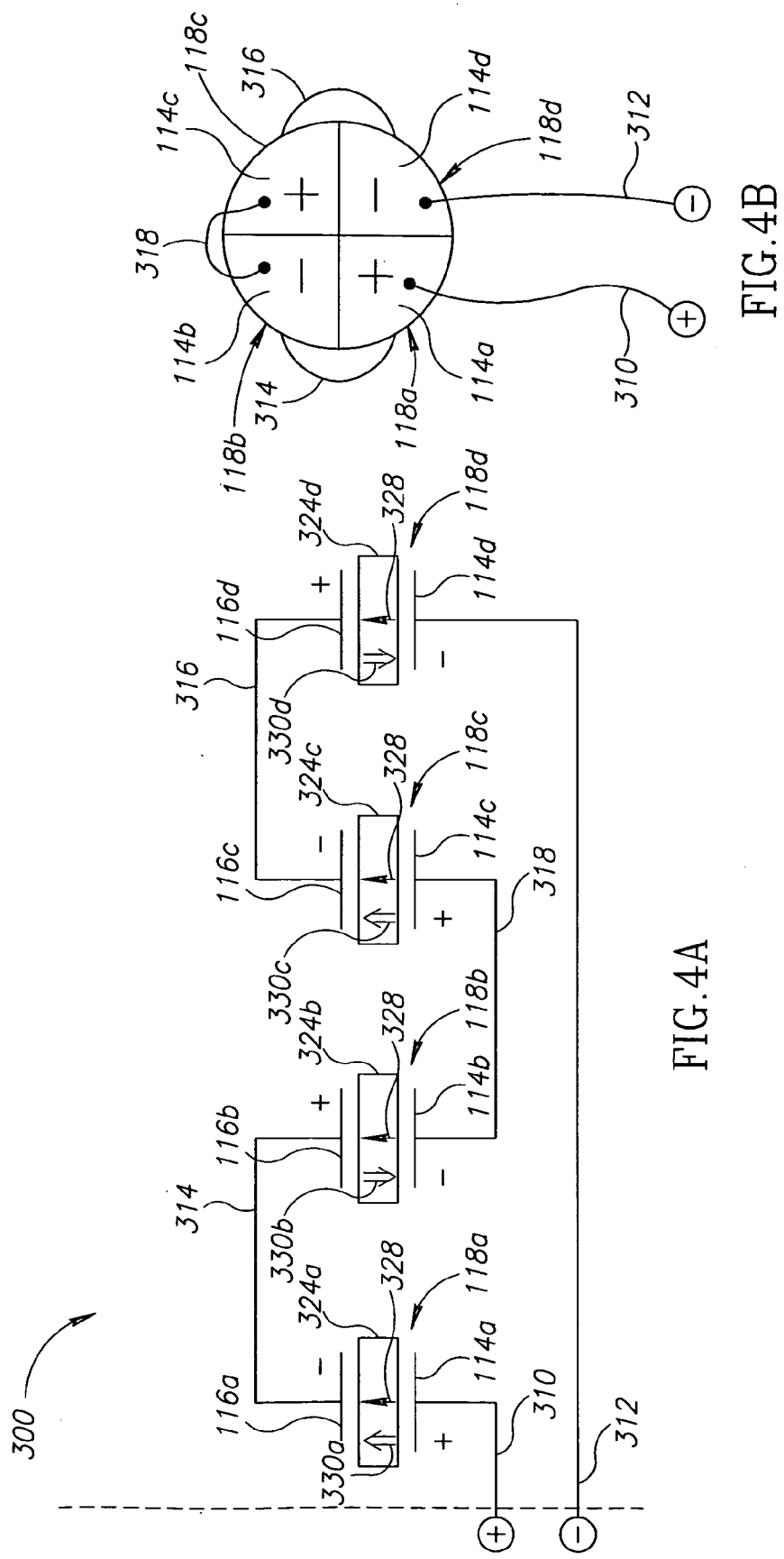

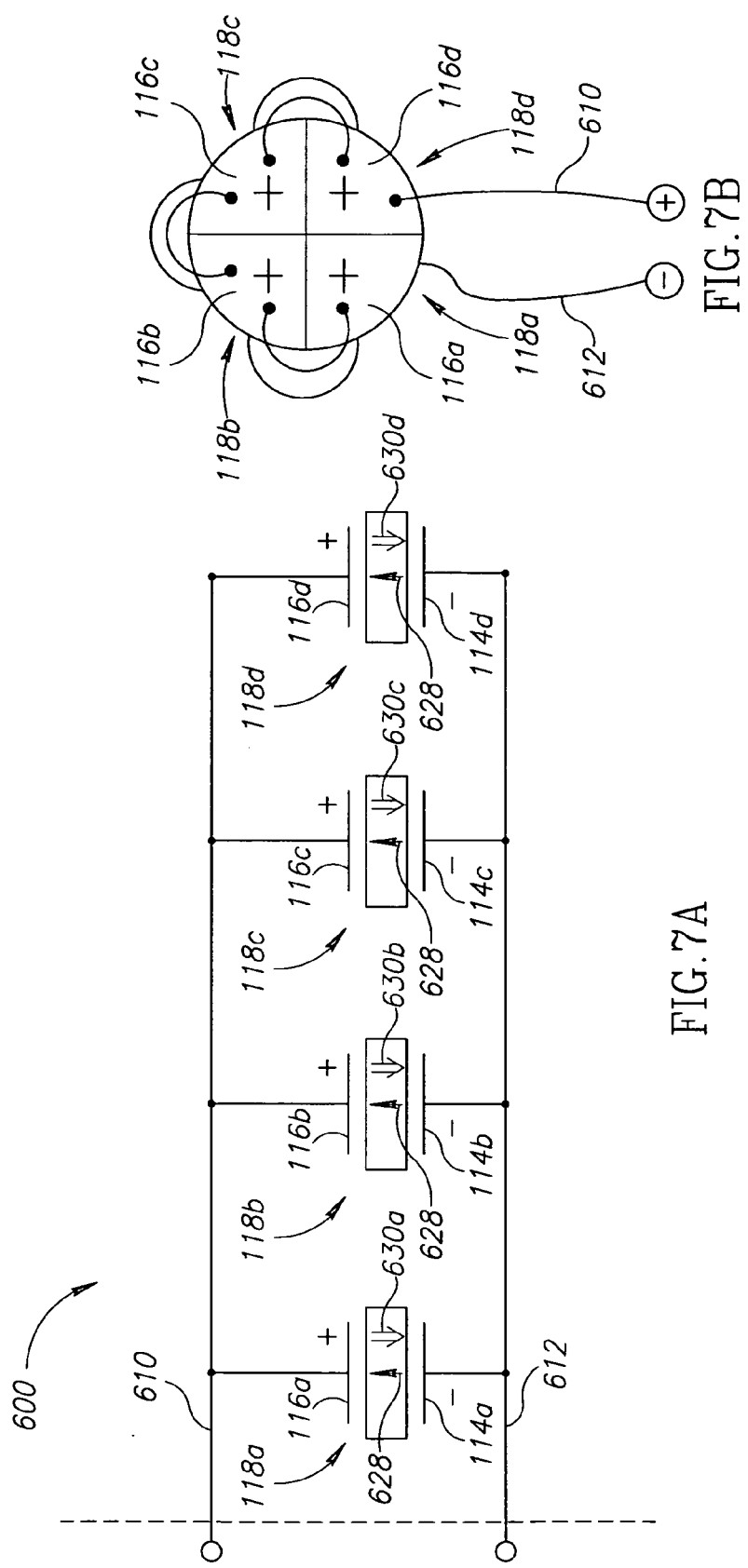

PATTERNED ULTRASONIC TRANSDUCERS

RELATED APPLICATIONS

This application claims the benefit of U.S. Provisional Patent Application No. 61/064,582, filed Mar. 13, 2008, which is incorporated herein by reference.

FIELD OF THE DISCLOSURE

The present disclosure relates to the field of transducers for use in ultrasonic treatment of tissue.

BACKGROUND

Ultrasound is widely used in medicine for diagnostic and therapeutic applications. Therapeutic ultrasound may induce a vast range of biological effects at very different exposure levels. At low levels, beneficial, reversible cellular effects can be produced, whereas at higher intensities, instantaneous cell death can occur. Accordingly, ultrasound therapies can be broadly divided into two groups: "high" power and "low" power therapies. At one end of the spectrum, high power applications include high intensity focused ultrasound (HIFU) and lithotripsy, while at the other end, low power applications comprise sonophoresis, sonoporation, gene therapy, bone healing, and the like.

A popular area in the field of aesthetic medicine is the removal of subcutaneous fat and the reduction of the volume of adipose tissue, resulting in the reshaping of body parts, frequently referred to as "body contouring". One such technique is a non-invasive ultrasound-based procedure for fat and adipose tissue removal. The treatment is based on the application of focused therapeutic ultrasound that selectively targets and disrupts fat cells without damaging neighboring structures. This may be achieved by, for example, a device, such as a transducer, that delivers focused ultrasound energy to the subcutaneous fat layer. Specific, pre-set ultrasound parameters are used in an attempt to ensure that only the fat cells within the treatment area are targeted and that neighboring structures such as blood vessels, nerves and connective tissue remain intact.

Focused high intensity acoustic energy is also used for therapeutic treatment of various medical conditions, including the non-invasive destruction of tumerous growths by tissue ablation and/or destruction.

For such medical and cosmetic purposes, it is often desirable to be able to focus the ultrasonic output of the transducer. To achieve this, transducers are often comprised of a cup-shaped piezoelectric ceramic shell with conductive layers forming a pair of electrodes covering the convex outside and concave inside of the piezoelectric shell. Typically, the transducers have the shape of a segment of a sphere, with the "open end" positioned toward the subject being treated.

The transducer is excited to vibrate and generate ultrasound by pulsing it, using a high frequency power supply generally operating at a resonant frequency of vibration of the piezoelectric material.

Such a spherical transducer exhibits an "axial focal pattern". This is an ellipsoidal pattern having a relatively small cross section and a relatively longer axis coincident with a "longitudinal" axis of the transducer, that is, a line through the center of rotation of the transducer perpendicular to the equatorial plane. However, to treat relatively large volumes of tissue, it would be generally advantageous to modify the focal pattern so that it is spread laterally and exhibits decreased intensity along the transducer axis.

Furthermore, since cosmetic treatments in particular, and efficient apparatus utilization in general, are sensitive to the time taken to perform the procedure, methods whereby a singly focused region is moved over the subject's body are unattractive commercially, and better efficacy of such treatments would be desirable.

Other types of transducers are planar in shape, generating a sheet of energy at the target plane, but the focusing power of such transducers is limited. Such planar transducers may also incorporate an acoustic lens to focus energy to a desired location.

Transducers which emit ultrasound in a single focused beam have limitations, such as requiring motion to scan over a treated area larger than their focal region, and such as being generally single-frequencied. This can be overcome by the use of transducer heads comprising several separate emitting sections. Such prior art, multiple segment transducers are generally constructed of a number of separate ceramic piezoelectric elements glued together, or epoxy embedded, in order to produce a single integrated head. However, transducers produced by such methods are generally costly to manufacture because of the labor intensive process of manufacture, and are often unreliable because of the susceptibility of the adhesive or epoxy matrix to loosen, degrade, or otherwise interfere with the transducers under the effects of high intensity ultrasound.

There therefore exists a need for a new transducer and method of manufacturing multi-segmented transducers, and methods of operating such transducers and transducer arrays and system, which will enable novel treatments to be achieved without the potential disadvantages of prior art adhesive-assembled transducers.

SUMMARY

The present disclosure seeks to provide a new segmented transducer structure, in which a single, unitary sample of piezoelectric material having two opposite surfaces is induced to operate as if it were composed of a plurality of smaller individual transducer segments, by means of separate electrode elements applied-to at least one of said opposite surfaces of the opposite surfaces, wherein each electrode element is associated with a transducer segment. The application of the electrode elements to the at least one surface can be performed either by dividing up a continuous electrode preformed on a surface of the material, generally by scribing or cutting the surface, or by applying a coating to the surface in the form of electrically separate electrode elements. Each of the separate electrode elements can then be activated separately by its own applied high frequency voltage, generally applied between the segment and an electrode on the opposing surface of the sample. Such a multi-element transducer has a structure which is simpler to construct than an adhesively assembled multi-element transducer, and which is also generally more reliable. The individual transducer segments generally operate independently of each other, and, other than some small effects on close neighbors, do not mutually interfere, thus enabling additive combinations of their outputs to be synthesized by appropriate excitation of the associated electrode elements. According to some embodiments of the present disclosure, the single component base transducer can be constructed to have separate regions of different vibrational frequency when excited, and the electrode elements arranged to overlie these separate regions, such that a multiple frequency ultrasound emission can be provided by exciting the separate electrode regions.

There is therefore provided, in accordance with an embodiment of the disclosure, a transducer array for lysing an adipose tissue, the transducer array comprising at least one unitary piece of piezoelectric material having first and second opposing surfaces; and one or more conductive layers on each of said first and second opposing surfaces, wherein at least one of said one or more conductive layers comprises a plurality of electrode elements.

There is further provided, in accordance with an embodiment of the disclosure, a transducer array for lysing an adipose tissue, the transducer array comprising at least one unitary element of piezoelectric material adapted to operate as a plurality of individual transducer segments.

In some embodiments, upon excitation of one of said electrode elements said piezoelectric material associated with said at least one electrode element is excited to emit ultrasound energy.

In some embodiments, said plurality of electrode elements is formed by dividing up a preformed conductive layer on said surface.

In some embodiments, said dividing up is performed by scribing, mechanical cutting, laser cutting or any combination thereof.

In some embodiments, said plurality of electrode elements is formed by depositing a conductive layer having a plurality of electrode elements onto said surface.

In some embodiments, said electrode elements are deposited by vapor deposition, sputtering, silk screen printing, painting or any combination thereof.

In some embodiments, said electrode elements are deposited through a mask.

In some embodiments, the transducer array is further adapted to receive voltage between said electrode elements on said first opposing surface and said conductive layer on said second opposing surface.

In some embodiments, said unitary piece of piezoelectric material has different segments of differing thickness.

In some embodiments, said plurality of electrode elements is located such that at least some of them essentially overlie at least some of said segments of differing thickness of said unitary piece of piezoelectric material.

In some embodiments, said different segments of differing thickness emit ultrasound at different frequencies when excited by an appropriate field, such that the frequency of said ultrasound energy emitted by said transducer is dependent on which of said electrode elements of said conductive layer are excited.

In some embodiments, said unitary piece of piezoelectric material has different segments of differing material characteristics.

In some embodiments, said plurality of electrode elements of said conductive layer is located such that at least some of them essentially overlie at least some of said segments of differing material characteristics of said unitary piece of piezoelectric material.

In some embodiments, said different segments of differing material characteristics emit ultrasound at different frequencies when excited by an appropriate field, such that the frequency of said ultrasound energy emitted by said transducer is dependent on which of said electrode elements of said conductive layer are excited.

In some embodiments, said piezoelectric material is a ceramic, and said different material characteristics are of different stoichiometric composition, different doping levels, different densities or any combination thereof.

In some embodiments, said transducer is adapted to focus ultrasound of different frequencies essentially simultaneously onto a single target area.

In some embodiments, said unitary piece of piezoelectric material has a form of any one of a hemisphere, a sphere, a spherically shaped cap, a curved cap, a half cylinder, a cylindrical shape and a flat plate.

In some embodiments, the transducer array is adapted to be used in a high intensity focused ultrasound (HIFU) application.

In some embodiments, the transducer array is adapted to be used in a low intensity focused ultrasound (LIFU) application.

In some embodiments, the transducer array is adapted to be used in a mid intensity focused ultrasound (MIFU) application.

There is further provided, in accordance with an embodiment of the disclosure, a system for lysing an adipose tissue, the system comprising a transducer array comprising at least one single element of piezoelectric material adapted to operate as a plurality of individual transducer segments; and a controller adapted to energize one or more of the plurality of individual transducer segments.

There is further provided, in accordance with an embodiment of the disclosure, a method of generating focused ultrasound energy for lysing of adipose tissues, the method comprising providing at least one unitary piece of piezoelectric material having first and second opposite surfaces and a conductive layer on each of said first and second opposite surfaces, wherein at least one of said conductive layers is divided up into a plurality of electrode elements; and applying an exciting voltage to at least one of said electrode elements on said first opposite surface and to said conductive layer on said second opposite surface, so as to excite said piezoelectric material in a vicinity of said at least one electrode element to emit ultrasound energy.

In some embodiments, said plurality of electrode elements is formed by dividing up a preformed conductive layer on said surface.

In some embodiments, said dividing up is performed by any one of scribing, mechanical cutting and laser cutting.

In some embodiments, said plurality of electrode elements is formed by depositing a conductive material onto said surface.

In some embodiments, said conductive material is deposited by any one of vapor deposition, sputtering, silk screen printing and painting.

In some embodiments, said conductive material is deposited through a mask.

There is further provided, in accordance with an embodiment of the disclosure, a method of generating focused ultrasound energy for lysing of adipose tissues, the method comprising providing at least one unitary element of piezoelectric material adapted to operate as a plurality of individual transducer segments wherein the individual transducer segments are adapted to be operated by exciting a plurality of electrode elements associated with said transducer segments, each electrode element defining an individual transducer segment, and applying voltage to at least one of said electrode elements and to an electrode on an opposing surface, such as to cause the individual transducer segment associated with the at least one electrode element to emit ultrasound energy.

There is further provided, in accordance with an embodiment of the disclosure, a method for lysing adipose tissue comprising energizing one or more of a plurality of individual transducer segments of a unitary piece transducer array; and transmitting focused ultrasound from the energized one or more of the plurality of individual transducer segments to a target area tissue of a subject body.

BRIEF DESCRIPTION OF THE FIGURES

The present disclosure will be understood and appreciated more fully from the following detailed description, taken in conjunction with the drawings in which:

FIGS. 4A to 4B illustrate electrical schematic diagrams, according to some embodiments;

FIGS. 7A to 7B illustrate electrical schematic wiring layouts, according to some embodiments;

DETAILED DESCRIPTION

Glossary

Figure 1A:
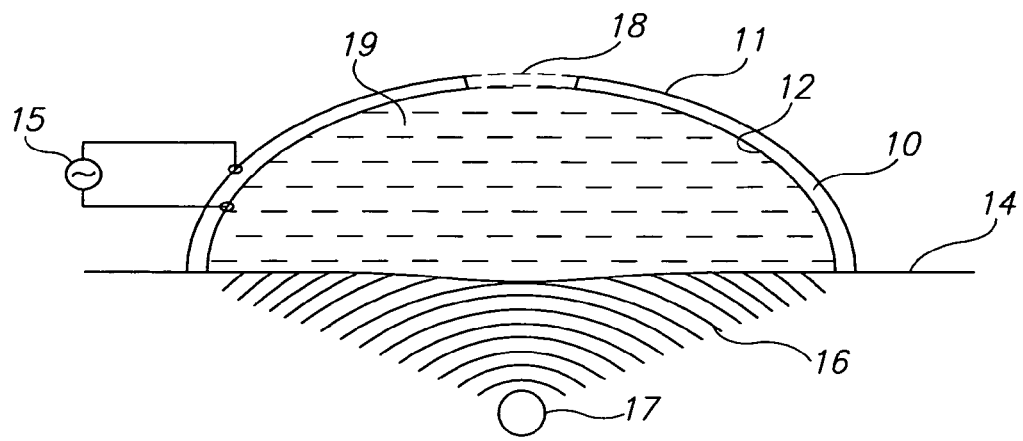
FIG. 1A shows schematically a cross sectional view of a prior art ultrasonic spherically shaped focusing piezoelectric transducer, being used to provide high intensity focused ultrasound (HIFU)

Below is presented a list of terms related to ultrasound equipment and ultrasonic output measurements which are used throughout the following disclosure:

As referred to herein, the term "Beam Axis" relates to a straight line joining the points of the maximum "Pulse Intensity Integral" measured at several different distances in the far field. This line is to be extended back to a transducer surface.

As referred to herein, the term "Beam Cross-Sectional Area" relates to the area on the surface of the plane, perpendicular to the "Beam Axis", consisting of all points where the acoustic pressure is greater than 50% of the maximum acoustic pressure in the plane.

As referred to herein, the term "Duty Cycle (DC)" relates to the ratio of "Pulse Duration" to "Pulse Repetition Period".

As referred to herein, the term "Focal Area" relates to the "Beam Cross-Sectional Area" on the "Focal Surface".

As referred to herein, the term "Focal Surface" relates to the surface which contains the smallest of all "Beam Cross-Sectional Areas" of a focusing transducer.

As referred to herein, the term "Intensity" relates to the ultrasonic power transmitted in the direction of acoustic wave propagation, per unit area normal to this direction, at the point considered.

As referred to herein, the term "Intensity, instantaneous (I)" relates to the instantaneous ultrasonic power transmitted in the direction of the acoustic wave propagation, per unit area normal to this direction, at the point considered. It is given in the far field by:

$$I=P^2/(\rho^*c),$$

wherein P is instantaneous acoustic pressure;
ρ is the density of the medium;
c is the speed of sound in the medium.
(Unit: W/cm$^2$)

As referred to herein, the term "Intensity, pulse-average (IPA)", measured in units of W/cm$^2$, relates to the ratio of the Pulse Intensity Integral (energy fluence per pulse) to the "Pulse Duration".

As referred to herein, the term "Intensity, spatial average, temporal average (ISATA)", measured in units of W/cm$^2$, relates to the temporal-averaged intensity averaged over the beam cross-sectional area.

As referred to herein, the term "Intensity, spatial-peak, pulse average (ISPPA)", measured in units of W/cm$^2$, relates to the value of the intensity pulse-average at the point in the acoustic field where the pulse-average intensity is a maximum or is a local maximum within a specified region.

As referred to herein, the term "Intensity, spatial-peak, temporal-average (ISPTA)", measured in units of W/cm$^2$, relates to the value of the temporal-average intensity at the point in the acoustic field where the temporal-average intensity is a maximum, or is a local maximum within a specified region.

As referred to herein, the term "Intensity, temporal-average (ITA)" relates to the time average of intensity at a point in space. The average is taken over one or more Pulse Repetition Periods.

As referred to herein, the term "Peak-rarefactional acoustic pressure (Pr)" relates to the Maximum of the modulus of the negative instantaneous acoustic pressure in an acoustic field.

As referred to herein, the term, "Pulse Duration (PD)", measured in units of time (seconds), relates to 1.25 times the interval between the time when the Pulse Intensity Integral at a point reaches 10 percent and 90 percent of its final value.

As referred to herein, the term "Pulse Intensity Integral (PII)", measured in units of W/cm$^2$, relates to the time integral of instantaneous intensity for any specific point and pulse, integrated over the time in which the envelope of acoustic pressure or hydrophone signal for the specific pulse is non-zero. It is equal to the energy fluence per pulse.

As referred to herein, the term "Pulse Repetition Period (PRT)" for a pulsed waveform, measured in units of W/cm$^2$, relates to the time interval between two successive pulses.

As referred to herein, the term "HIFU" relates to High Intensity Focused Ultrasound—the use of high intensity focused ultrasound energy in ultrasound treatment (therapy). Ultrasound treatment may induce a vast range of biological effects at different exposure levels. At low levels, essentially reversible cellular effects can be produced, whereas at higher intensities, instantaneous cell death may occur. Accordingly, ultrasound therapies may be broadly divided into two groups: "high" power and "low" power therapies. At the one end of the spectrum, high power therapies include, for example, high intensity focused ultrasound (HIFU) and/or lithotripsy, while at the other end, low power therapies comprise, for example, sonophoresis, sonoporation, gene therapy and/or bone healing. According to some embodiments, the term HIFU may further encompass MIFU and/or LIFU.

As referred to herein, the term "MIFU" relates to Mid Intensity Focused Ultrasound—the use of medium intensity focused ultrasound energy in ultrasound treatment.

As referred to herein, the term "LIFU" relates to Low Intensity Focused Ultrasound—the use of low intensity focused ultrasound energy in ultrasound treatment.

As referred to herein, the terms "transducing elements", "transducing segments" and "transducing zones" may interchangeably be used. The terms relate to different regions/zones on a unitary transducer acting as individual transducers.

As referred to herein, by the terms "exciting electrode element" and "apply exciting voltage to a electrode element" it is meant that there always exists a second ("ground") electrode on the opposite surface to which the same voltage, but with the opposite sign, is applied.

As referred to herein, the terms "segmented electrode", "segmented conductive layer" or "segmented layer" refer to a plurality of electrically isolated conductive electrode elements disposed on at least one of two opposite surfaces of one unitary piece of piezoelectric material.

As referred to herein, the term "conductive layer" may include uniform area(s), non-uniform area(s), continuous area(s), non-continuous area(s), or any combination thereof. The term "conductive layer" is usually not limited to a layer which is necessarily conductive along its entire area; in some embodiments, a conductive layer may be a deposit of a conductive material that may be segmented earlier or later in the process, so that it is not necessarily conductive throughout.

As referred to herein, the terms "electrode" may sometimes, when described so explicitly or implicitly, refer to a segmented layer of conductive material including multiple "electrode elements", electrically separate from one another. For example, such an electrode may be referred to as a "segmented electrode".

In common with diagnostic ultrasound, therapeutic ultrasound exposures can be described in terms of either the acoustic pressure or the intensity. The description of intensity for pulsed ultrasound may lead to some ambiguity. The acoustic pressure in the acoustic field is by itself spatially variant, and the pulsed shape of the signal induces additional temporal variations. It is possible to calculate intensities based on the maximum pressure measured in the field or based on a pressure averaged over a specified area. When describing the energy delivery, it is also necessary to distinguish whether the intensity is averaged only when the pulse is "on" (the pulse average) or over a longer time, which includes "on" and "off" times (temporal average). A number of different parameters related to intensity may be used. The most usual ones, defined in a number of standards (such as listed by: NEMA Standards Publication UD 2-1992, entitled "Acoustic Output Measurement Standard for Diagnostic Ultrasound Equipment" (1992), incorporated herein by reference, in its entirety), are ISPTA, ISPPA and ISATA. When cavitation is the predominant mechanism, peak negative pressure is usually considered the parameter of most relevance. Table 1 hereinbelow provides a classification of ultrasound field characteristics for different applications based on values of ISPTA, frequency and pressure. The data in Table 1 is based on data from A. Shaw, et al, "Requirements for Measurement Standards in High Intensity Focused Ultrasound (HIFU) Fields", NPL Report DQL AC 015, National Physical laboratory, Middlesex, UK, February 2006 and V. F. Hamphrey, "Ultrasound and Matter—Physical Interactions", Progress in Biophysics and Molecular Biology, 93, 195-211, 2007, both incorporated herein by reference, in their entirety.

TABLE 1

| Modality | Frequency range, MHz | Pressure (P$_r$), MPa | Intensity ISPTA, W/cm$^2$ |
|---|---|---|---|
| Diagnostic B-mode | 1-15 | 0.45-5.5 | 0.0003-0.99 |
| Diagnostic CW Doppler | 1-10 | 0.65-5.3 | 0.17-9.1 |
| Bone growth stimulation | 1.0-1.5 | 0.05 | 0.03 |
| Physiotherapy | 0.75-3.4 | 0.5 | <3 |
| Drug delivery | Up to 2.0 | 0.2-8.0 | Various intensities |
| HIFU thermal | 0.8-2.0 | 10 | 400-10000 |
| HIFU histotripsy | 0.7-1.1 | 22 | 200-700 |
| Haemostasis | 1-10 | 7 | Up to 5000 |
| Lithotripsy | 0.5 | 10-15 | Very low, <10-4 |

In general, there are a few ways by which ultrasonic waves may influence a tissue with which they interact: thermal (heating) effects, and/or mechanical effects (such as, for example, shearing forces, cavitation, and the like), as further detailed below.

Several therapeutic ultrasonic applications use heating to achieve a required effect. In the case of "low power" ultrasound, raising the temperatures above normothermic levels by a few degrees may have a number of beneficial effects, such as, for example, increasing the blood supply to the affected area. In case of "high power" ultrasound applications, tissue temperature are raised very rapidly (typically in less than 3 seconds) to temperatures in excess of 56° C. This may usually cause instantaneous cell death. For example, hyperthermia treatments rely on cells being held at temperatures of 43-50° C. for times up to an hour, which may lead to the inability of cells to divide. The magnitude of the temperature rise depends on the ultrasound intensity, the acoustic absorption coefficient of exposed tissue, tissue perfusion and time for which the sound is "on". The temperature increase due to ultrasound absorption can be calculated by using Pennes bio-heat equation (H. H. Pennes, "Analysis of tissue and arterial blood temperatures in the resting human forearm", J. Appl. Physiol. 1, 93-122, 1948, incorporated herein by reference, in its entirety:

$$\frac{dT}{dt} = k\nabla^2 T - \frac{(T - T_0)}{\tau} + \frac{q_v}{\rho_0 C_P}$$

wherein, k is the thermal diffusivity, $\tau$ is the time constant for the perfusion, $T_0$ is the initial (ambient) temperature, $q_v$ is the heat source distribution and Cp is the specific heat capacity of the medium at constant pressure. The first term on the right-hand side of Pennes' bio-heat equation accounts for diffusion using the gradient of temperature while the second term accounts for perfusion using the diffusion time constant.

In general, the heat source term q, is very complex, as it depends on the nature of the field produced by the transmitting transducer, which may be, for example, focusing. There exist a number of approaches for calculating $q_v$. One of them, which is valid even for strongly focusing transducers and high amplitude values, is described, for example, in Goland, et. al., "Strongly Curved Short Focus Annular Array For Therapeutic Applications," in *Proceedings of the 2006 IEEE International Ultrasonics Symposium.*, 2345-2348, Vancouver, 2006, the content of which is incorporated herein by reference, in its entirety.

Several therapeutic ultrasonic applications use mechanical effects to achieve desired results. The most prominent of the mechanical effects are shearing force (stress) and cavitation. The term cavitation generally refers to a range of complex phenomena that involve the creation, oscillation, growth and collapse of bubbles within a medium. The cavitation behavior depends on the frequency, pressure, amplitude, bubble radius and environment. For example, lithotripsy therapeutic procedure uses focused shock waves at very high acoustic pressure for destroying stones in kidneys. Since in this application the repetition frequency of pulses is very low (at about 1 Hz), there is no noticeable heating during the treatment, and the produced effect can be considered as solely mechanical. Another example of the mechanical effect related to cavitation is histotripsy procedure, which is defined as mechanical fractionation of soft tissue by applying high-amplitude acoustic pulses with low temporal-average intensities. Its mechanism is a non-thermal initiation and maintenance of dynamically changing "bubble clouds"—a special form of cavitation, which is used for precisely destroying tissue such as in cardiac ablation.

When the signal amplitude is under the cavitation threshold but still high enough, then shear stresses may be responsible for biological effects. It has been previously shown (For example, by Burov et. al., "Nonlinear Ultrasound: Breakdown of Microscopic Biological Structures and Nonthermal Impact on a Malignant Tumor", Doclady Biochemistry and Biophysics, 383, 101-104, 2002, the content of which is incorporated herein by reference in its entirety) that exposure of cells to high power ultrasonic radiation under the conditions excluding thermal and cavitation-induced degradation, was accompanied by structural modification of macromolecules, membranes, nuclei and intracellular submicroscopic complexes. Some of the mechanisms that were suggested to explain these phenomena are: large shear stresses generated in the thin acoustic interface near solid boundaries, forces of friction between large-mass macromolecules and surrounding oscillating liquid, acoustic microscopic flows, or any combination thereof.

A parameter that allows estimating the likelihood of cavitation is called Mechanical Index (MI) and is defined as:

$$MI = \frac{P_r}{\sqrt{f}}$$

wherein Pr is the peak rarefactional pressure of the acoustic signal in MPa and f is the frequency of the signal in MHz. The American Institute of Ultrasound in Medicine (AIUM), National Electrical Manufacturers Association (NEMA) and FDA adopted the Mechanical Index as a real time output display to estimate the potential for cavitation during diagnostic ultrasound scanning (Standard for Real-Time Display of Thermal and Mechanical Acoustic Output Indices on Diagnostic Ultrasound Equipment, second ed. AIUM, Rockville, 1998, incorporated herein by reference). The assumption is that if one does not reach the threshold MI=0.7, then the probability of cavitation is negligible. The maximum value of MI that is allowed for diagnostic machines seeking approval in the USA is 1.9. For example, it has been previously shown experimentally, that MI values which correspond to a cavitation threshold at a frequency of, for example, 0.2 MHz, have values from 3.4 to 7.8, depending on tissue type and characteristics.

Therefore, it may be understood that, by choosing the appropriate set of signal parameters, one can expose tissue in "thermal" and/or "mechanical" mode, causing various or completely different effects. If, for example, the signal amplitude will be under the cavitation threshold, but the energy is delivered in continuous mode (CW), or at high DC values, then the effect may be mostly thermal. At high ISPTA values, coagulation and necrosis of tissues may be caused. By changing DC values, it is possible to vary temperature limits and its rise rate in a wide range. By contrast, by choosing very high signal amplitudes (over the cavitation threshold) and very low DC, it is possible to produce mechanical effects causing negligible heating. At high ISPPA and low ISPTA values, one can achieve complete tissue emulsification without heating. Tissue debris size in this case may be as little as 2 µm. Hence, selection/use of appropriate parameters may permit selective formation of cavitation in target tissue but not in neighboring tissues.

Ultrasonic energy can be non-invasively delivered to the tissue in either a non-focused or focused manner. In the first case, tissue is exposed to approximately the same extent, beginning from the skin and down to a certain depth. Due to ultrasound attenuation in the tissue, the signal energy will decrease with distance so that the maximum intensity will be on the skin. Beam divergence for non-focused ultrasound is very low; it begins to increase only from distances $Z>d^2f/4c$ from the radiator surface, wherein d is a characteristic dimension of the radiator (such as a diameter). For example, for a radiator having a diameter of 30 mm and working at 1.0 MHz, this distance will be of about 150 mm. This means that the ultrasound energy targets non-selectively all types of tissue (such as skin, subcutaneous fat, muscles, and so forth) within the cylinder with a diameter of 30 mm and a height of at least 150 mm. The maximal energy that could be delivered at a certain depth (where the effect is sought for) is limited by the levels, which are considered safe for surrounding tissues (including skin). Focused ultrasound allows overcoming these problems by concentrating most of the energy in the focal area, where the intensity is significantly higher than in the surrounding tissue.

Reference is now made to FIG. 1A, which illustrates schematically a cross sectional view of a prior art ultrasonic spherically shaped focusing piezoelectric transducer 10, typically being used to provide high intensity focused ultrasound (HIFU) to lyse adipose tissue in a tissue region of a patient's body below the patient's skin 14. The transducer 10 may be produced using any of various methods and devices known in the art, and is formed having electrode elements 11, 12, in the form of thin conducting coatings on its surfaces. The transducer is driven by means of a high frequency power source 15, which applies a voltage between the electrode elements 11, 12, of the transducer, thus exciting resonant vibration modes of the transducer, and generating high intensity ultrasound waves for killing, damaging or destroying adipose tissue. The transducer is optionally filled with a suitable coupling material 19 for acoustically coupling the transducer to the patient's skin 14. A commonly used material is a gel. Because of the concave shape of the transducer, the ultrasound waves are focused 16 towards a focal region 17, which is generally in the form of an ellipsoid, having its major axis along the wave propagation direction. The size of this focused region is dependent on a number of factors, mainly the curvature of the transducer, and the frequency of ultrasound emitted, varying for a transducer on the order of 70 mm diameter, from an ovoid of approximately 7 mm×5 mm for a frequency of 200 kHz, to approximately 3 mm×1.5 mm for 1 MHz ultrasound. A hole 18 is provided at the apex of the transducer, for placing an imaging transducer for monitoring acoustic contact and/or treatment efficiency during use of the transducer. It is to be understood however, that this monitoring can also be accomplished by using any of the electrode elements of the array, such that the central hole monitor is only one method of performing the monitoring, and where optionally illustrated in any of the drawings, is not meant to limit the transducer shape shown.

The frequency of the emitted ultrasound, for a transducer of a given shape, material and diameter, is mainly dependent on the thickness of the shell. For instance, for an 84 mm diameter cap-shaped transducer similar to that shown in FIG. 1A, for a thickness of 8.4 mm, a transducer using a ceramic of the type APC841, supplied by Americam Piezo Ceramics, Inc., PA, USA, will emit at a frequency on the order of 200 kHz., while for a thickness of 1.7 mm, the transducer will be excited at a frequency on the order of 1 MHz.

Figure 1B:
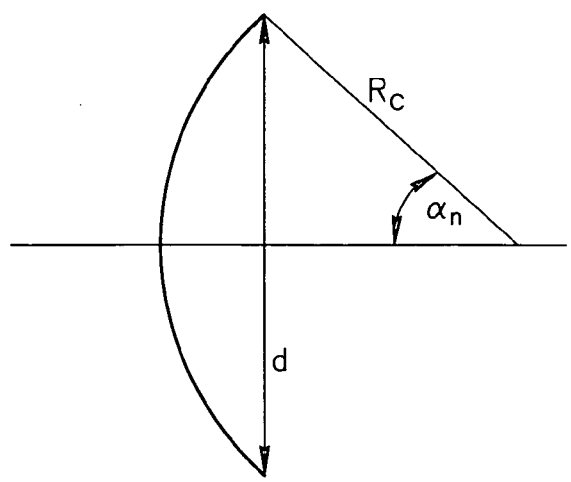
FIG. 1B schematically illustrates a spherical segment transducer.

Furthermore, considering the schematic half-spherical transducer of FIG. 1B, having aperture diameter d, radius of curvature Rc and working frequency f, the expression for pressure gain $K_P$, which is a ratio of pressure $P_F$ in the focus to pressure $P_S$ on the radiator surface may be provided by the formula:

$$K_p = \frac{P_F}{P_S} = \frac{2\pi \cdot f R_c}{c}(1 - \cos\alpha_n)$$

Wherein $\alpha_n$ is a half-aperture angle. Analysis of the equation demonstrate that it is possible to increase the gain by increasing either f or $\alpha_m$ or both. For example, a radiator with d=100 mm and Rc=100 mm will have Kp=11 at frequency 0.2 MHz and Kp=55 at 1.0 MHz.

As mentioned above, interaction of the focused ultrasound waves with the tissue on which they are focused is dependent on a number of factors: thermal effects, which usually result in coagulation of the tissue, and are non-selective, the acoustic energy affecting whatever tissue it encounters at a power density at which the effects take place; rupture or mechanical effects, which tear the cell walls, thus damaging the cell structure itself. This may not destroy the cell immediately, but may damage it sufficiently that it dies within a period following the treatment. This may be hours or days, depending on the extent and type of damage inflicted. This phenomenon is generally highly selective with regard to the type of tissue on which the ultrasound impinges, but it requires a high level of energy on target to be effective. Such mechanical effects may include streaming, shear or tensional forces; and cavitation effects, in which small bubbles are formed within the tissue.

The treatment time per patient, using a current, state-of-the-art, roving focusing ultrasonic head, such as the one illustrated in FIG. 1A, treating successive regions at a time, is typically 90 minutes, and may involve almost 1,000 treatment nodes to cover an adult abdomen, each spot taking approximately 6 seconds. Generally, only about half of this 6 second period may be spent in actual treatment, the rest of the time being used for moving and positioning the treatment head. For reasons of commercial efficacy, and for reasons of patient acceptance, it would be highly desirable to significantly decrease this time. Prior art methods of achieving this generally rely on increasing the total energy of ultrasound applied to the tissue, thus reducing the time needed to achieve the desired effect. There are a number of ways of doing this, such as, for example: increasing the exciting voltage applied to the transducer, which increases the intensity of the ultrasound waves emitted; increasing the duty cycle of the pulses in the pulse train applied, to provide higher averaged power; and the like.

Certain applications of some of these methods are known in the art. However, it is not always possible or desirable to increase the operating frequency because sound attenuation increases with higher frequencies, and this may lead to higher heating and decreasing of a penetration depth of the ultrasound. In addition, since focal area dimensions are of the order of magnitude of the wavelength, higher frequencies produce smaller focal areas, thus limiting treatment abilities. Increasing the half-aperture angle an (FIG. 1B) requires enlargement of the transducer, making it more heavy and expensive, and less suitable for work. Moreover, the methods described above generally result in increased cavitation, or increased thermal effects, both of which are non-selective and hence may be dangerous to organs and/or tissue which are in close proximity to the treatment region. Furthermore, both these effects ultimately involve increased pain to the patient, which may make the treatment unacceptable. One prior art system utilizing a planar applicator, which results in a sheet of tissue being treated, in order to achieve faster results, operates intentionally in the thermal damage range of power, such that the patient's skin has to be continuously locally anesthetized for the treatment to be bearable.

Further methods of increasing the efficacy of the treatment may obtained by using the phenomenon known as Time Reversal, as further expounded in applicants' U.S. patent application Ser. No. 12/003,811, entitled "Time Reversal Ultrasound Focusing".

There are potential advantages to the variously available HIFU procedures, in the use of a number of separate transducers, each of which can be excited separately, rather than using a single transducer working in a single mode of operation. The advantages of treatment with a multiple transducer head are delineated in applicants' U.S. Provisional Patent Application No. 61/064,581, entitled "Operation of Patterned Ultrasonic Transducers".

There exist a number of methods of constructing such multiple transducer ultrasound heads. One of the simplest is to simply construct the spherical emitter out of a number of assembled segments of separate transducers. Additionally, in U.S. Pat. No. 7,273,459 for "Vortex Transducer" to C. S. Desilets et. al., incorporated herein by reference, there is described a method by which a multiple transducer head is produced by embedding a large number of separate transducer elements, each diced from a single transducer, in a matrix of epoxy.

Such methods of construction may generally be costly, time consuming, may possibly have a limited yield, and, because of the loosening effect of high intensity ultrasound on the glue or epoxy, may have limited lifetime. Furthermore, the adhesive may also absorb part of the ultrasonic energy, thus limiting power efficiency.

Reference is now made to FIG. 2, which schematically illustrates exemplary transducer head(s), wherein the transducer is divided into a plurality of transducer elements, and simultaneously exciting different transducer elements with AC voltages having different phases, according to some embodiments. Shown in FIG. 2A is a perspective drawing, with a portion cut away, which shows the structure of a multi-element, cup-shaped focusing transducer 1000 in schematic form. Transducer 1000 is comprised of a shaped ceramic body 1010, and bottom and top layers forming electrically conductive surfaces 1014 and 1016, respectively, on the concave inner and convex outer sides 1006 and 1008 of body 1010. Surfaces 1014 and 1016 may comprise conductive metal layers painted onto or otherwise applied to ceramic body 1010, for example, by spraying or by dripping conductive paint onto the piezoelectric body 1010 while spinning it, as further detailed below. A longitudinal axis of the transducer is indicated at 1030. The equatorial plane is indicated at 1032. For simplicity, transducer 1000 is described as spherical, but it should be understood that the transducer can be configured as a spherical cap, less than a hemisphere, and that other non-spherical configurations are also possible, as further demonstrated below. For example, the separate transducer elements are optionally created by scoring through the top and bottom conductive surfaces 1016 and 1014, for example, along meridians of the hemisphere, or in any other desired pattern, to create electrically isolated electrode element pairs. In the example shown in FIG. 2A, transducer 1000 is comprised of four transducer elements 1018a-1018d. Score lines 1020a-1020d extend completely through conductive layer 1016 to form spherical triangles that define outer electrode elements 1016a-1016d, respectively. Similar score lines (not visible in FIG. 1) extending completely through inner conductive layer 1014, and aligned with score lines 1020a-1020d, define the inner electrode elements. An axial opening 1024 at the top pole of the transducer body is ordinarily also provided to facilitate manufacturing, and to allow insertion of other medical instruments or sensors during use, such as, for example, an A-mode acoustic contact sensor, further detailed below. Appropriate wiring (not shown) connects the respective electrode element pairs to a suitable power supply or power supplies. When so configured and connected, the portions of the piezoelectric material between the respective electrode element pairs effectively function as separate transducers. If the exciting voltages for the adjacent transducer elements are of opposite phase, the resulting composite focal pattern is "circumferential"—meaning that it exhibits substantially zero ultrasound pressure along transducer axis 1030 and peaks in ultrasound pressure for each element symmetrically located along the circumference of a circle having its center along axis 1030. Referring to FIG. 2B, there is shown an enlarged vertical cross-sectional view of transducer 1000 illustrated in FIG. 2A. Again, for convenient description, it is assumed that transducer 1000 is spherical (with the longitudinal axis indicated at 1030, and the equatorial plane indicated at 1032), but it should be understood that a spherical cap or other curvatures are also encompassed within the scope of the disclosure. Transducer elements 1018a and 1018d shown in FIG. 2A are illustrated in FIG. 2B. As will therefore be appreciated, the drawing is sectioned along score lines 1020a and 1020b (see FIG. 2A). As illustrated, terminals 1026 and 1027 are connected respectively to the outer electrode elements 1016a, 1016d, and 1014a, 1014d, by which the transducer elements 1018a-1018d are energized. It should also be appreciated that the outer side 1034 of transducer 1000 (that is, the convex side) is conventionally anchored to a suitable mass so that the ultrasound energy emitted by the transducer is mainly directed from the inner, that is, concave side 1036, toward the subject under treatment. As mentioned herein, and as known by those skilled in the art, if materials such as PZT are exposed during manufacture to a high-strength electric (polling) field under appropriate conditions, the material will become polarized, that is, it will exhibit an overall orientation of positive and negative electric charge pairs in the crystal structure of the material which orientation is retained after manufacture. Then, if exposed to an electric field, the material may expand or contract, depending on the direction of the field relative to the direction of polarization. The diametrically extending arrows 1028 in FIG. 2A within piezoelectric material 1010 schematically indicate polarization direction. For an electric field generated in material 1010 parallel or anti-parallel to the polarization direction, the material respectively expands or contracts along the polarization direction. Reference is therefore made to FIG. 2C which illustrates schematically, a multiple transducer head, constructed according to an embodiment of the present disclosure, which utilizes a single ceramic element, virtually divided into separately emitting sub-transducers by means of dividing one of the exciting electrodes into separate elements. In FIG. 2C, there is shown a cross sectional view of a spherical ultrasound transducer 20, comprising a piezoelectric ceramic material which emits the ultrasound waves when excited. One surface of the transducer 20 may have a continuous conducting electrode, 21, while the electrode on the opposite side may comprise a number of electrically separate electrode elements 22, each of which may be excited by application of the appropriate predetermined high frequency voltage by means of connecting leads 23. In FIG. 2C, for clarity, the exciting source 24 is shown connected to only one of those electrode elements, although it is to be understood that each of the electrode elements should be so connected, either each independently of the others to its own high frequency voltage source, or alternatively, together with several groups of electrode elements, each group being connected to a separate source, or alternatively, together with all of the other electrode elements, all being connected to a single source. The voltage source or sources may be activated by means of a controller 26, which may be programmed to emit pulses for a predetermined length of time and at a predetermined rate and duty cycle commensurate with the treatment being performed. For convenience, it is the outer electrode of the arrangement of FIG. 2C which is shown segmented 22, this enabling simpler application of the exciting power, although it is to be understood that the disclosure will operate equally well with the inner electrode 21 segmented. It is even possible for both of the electrodes to be segmented, inner and outer segments generally being arranged opposite each other; but this arrangement may unduly complicate the electrical connection requirements.

The production of the separate electrode elements can be achieved by any of the methods known in the art. One such method is the coating of a continuous conductive layer, followed by mechanical scribing of the layer, whether the scribing is such that it penetrates into the ceramic surface itself, as shown in scribe marks 30 which penetrate into a ceramic surface 32, or whether the scribing only cuts the electrode into its separate elements, as shown in electrode elements 31, both as shown schematically in the embodiment of FIG. 2D. The scribing process can be performed on the segmented electrode surface only, or on both surfaces. This process can be a mechanical scribing or cutting process, or an ablating process, such as can be efficiently and rapidly performed using a CNC controlled laser scribing machine.

Alternatively, the electrode elements can be applied in an already segmented form by any of the methods known in the art, such as by silk screen printing, by spray or brush or roller painting or by vapor deposition or sputtering through a mask.

By this means, the electrode elements can be applied in a particularly cost effective manner, since all of the separate electrode elements are formed in a single procedure. Furthermore, the electrode elements can be readily applied on a base transducer having any shape or profile, whether spherical, flat, cylindrical or the like. All that is required is a suitably shaped mask to fit to the contour of the transducer surface on which the electrode elements are to be coated. Additionally, because of the blanket method of generating the electrode elements in a single process, there is no limit to the number of electrode elements, which can be produced, in contrast to prior art methods where each segment requires individual handling. It therefore becomes practical to make transducer heads with very large numbers of segments, which increases the flexibility and accuracy with which the various applications of the present disclosure can be performed.

Figure 2A:
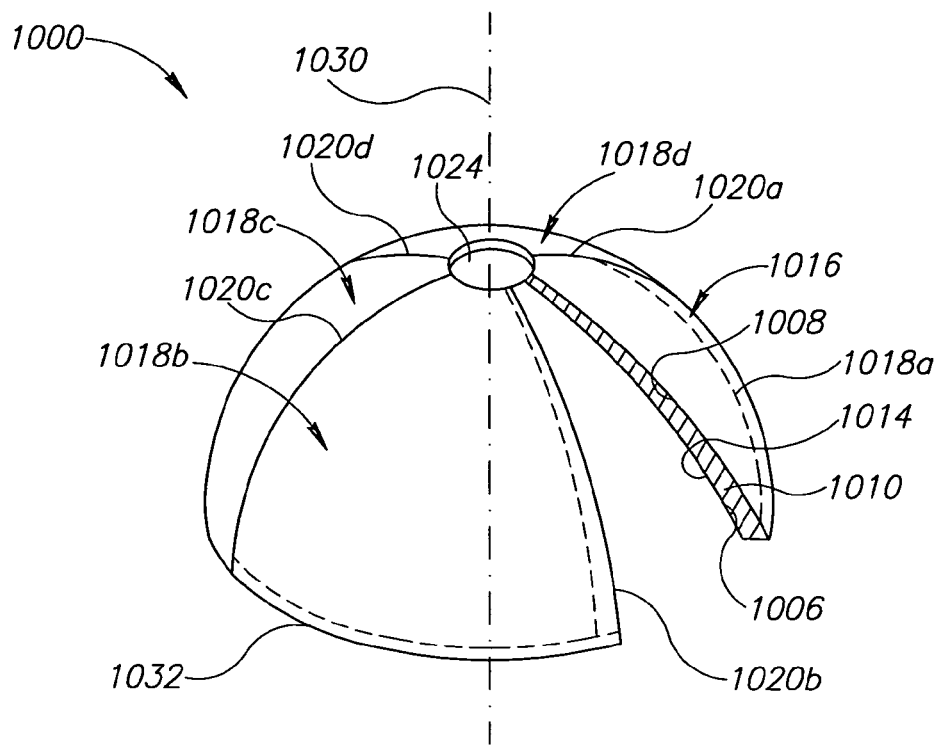
FIGS. 2A to 2D illustrate schematically different embodiments of a multiple transducer head, comprising a single spherical ceramic element having a segmented electrode.
Figure 2B:
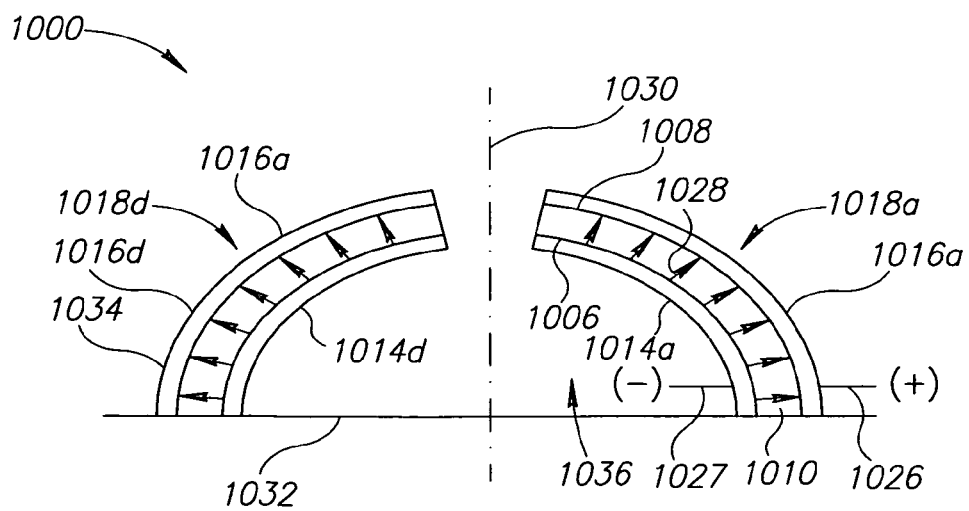
Figure 2C:
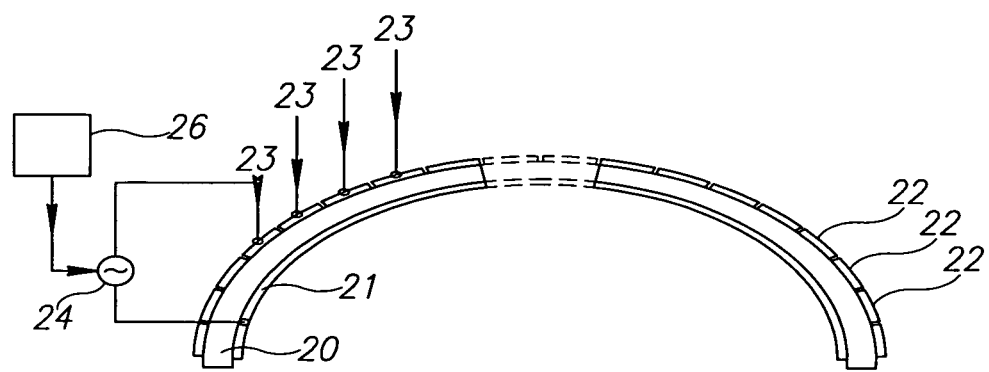
Figure 2D:
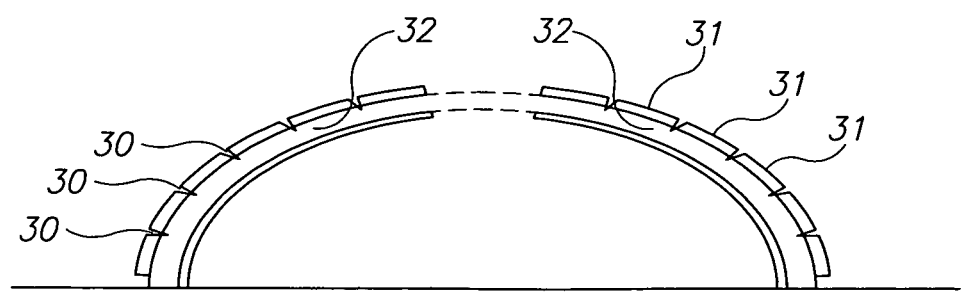
Figure 3A:
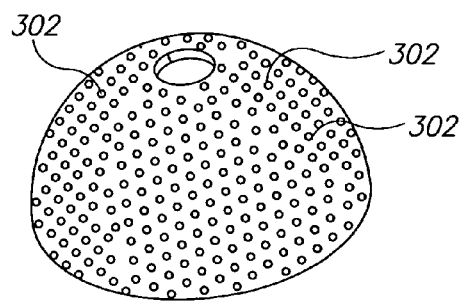
FIGS. 3A to 3F show schematically various differently shaped transducer heads, each constructed using a multi-element electrode on one or more unitary ceramic base transducers.
Figure 3B:
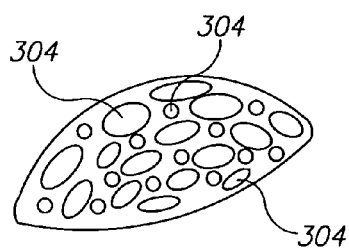
Figure 3C:
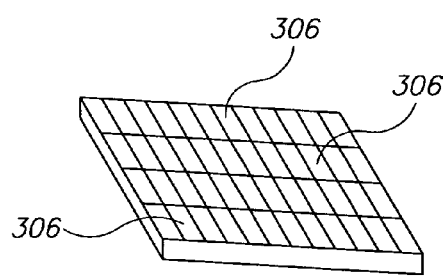
Figure 3D:
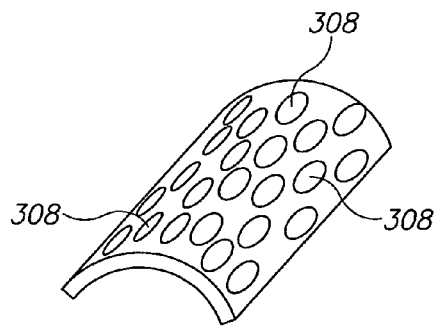

Reference is now made to FIGS. 3A to 3F, which illustrate schematic views of various differently shaped transducers, each comprising a single unitary piece of ceramic as the base, and having electrode elements on one of its surfaces. FIG. 3A shows an isometric view of the cup shaped embodiment of FIG. 2C, showing a plurality of circular segments, such as segments 302; FIG. 3B is a similar embodiment but showing how segments of different size, such as segments 304, can also be used; FIG. 3C shows a flat transducer having segments such as segments 306; and FIG. 3D shows a cylindrically shaped transducer having segments such as segments 308. The cylindrical embodiment of FIG. 3D provides a line of focused energy instead of a spot, and this may be useful for treatments performed on the arm or leg of a subject. It is to be understood that the arrangement of segments can be of shapes other than circular, can be randomly or regularly positioned, or can be loose-packed or close-packed or tiled, without departing from the present disclosure. Thus, in the embodiment of FIG. 3C, the electrode elements are shown in the form of a tiled rectangular array, which could be produced by simply scribing the rectangular lattice on the coated electrode, or by coating through a rectangular lattice. Such tiled arrangements utilize essentially all of the area of the transducer surface. Other tiled arrangements could also be used, such as squares, triangles (alternately inverted), hexagons and others. In addition, the use of various patterns and shapes such as circles, ovals, octagons, and the like, which do not form tiled structures, may also be used and may result in at least partial utilization of the transducer surface area.

Figure 3E:
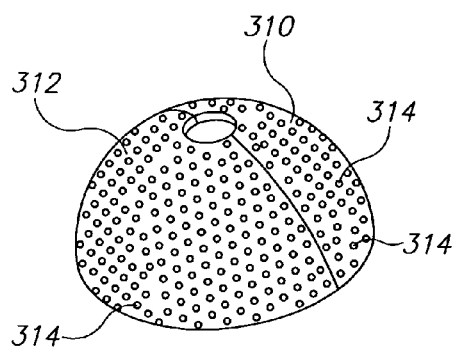

Furthermore, although the transducer head is most simply constructed using a single piece of piezoelectric material for the base element, as shown in the embodiments of FIGS. 3A to 3D, there may be applications or head shapes or sizes which make it preferable for the base element to be constructed of more than one piece of piezoelectric material, such as is shown in FIG. 3E, where the base element is made of two pieces of piezoelectric material 310, 312, each of which is separately divided into sub-transducers by means of the electrode element arrangement of the present disclosure, shown at segments such as segments 314. Likewise, the head could comprise an array of separate transducer elements, each of the separate elements being itself made up of a single unitary piece of transducer material, operated as a multi-transducer by virtue of the multiple electrode elements coated on it.

Figure 3F:
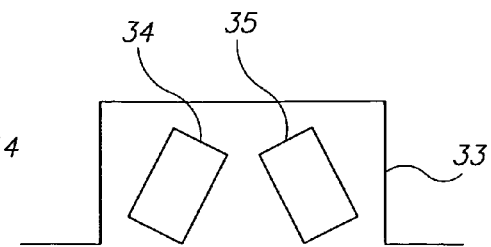

Reference is also made to FIG. 3F, which illustrates a head 33, made of two completely separated transducers 34, 35, which are operated in co-ordination to produce the desired focusing effects.

In the following description of FIGS. 4-8, the term "electrode" may refer to any electrode element or non-segmented, unitary electrode.

Reference is now made to FIG. 4, which schematically illustrates an electrical diagram of a multi-element transducer, according to some embodiments. FIG. 4A shows an electrical schematic diagram of a transducer 300 having four transducer elements 118a-118d. Element 118a, for example, is comprised of inner electrode 114a, outer electrode 116a, and an intervening portion 324a of shaped piezoelectric body 110 (see FIGS. 1 and 2). Respective transducer elements 118b-118d are comprised of inner electrodes 114b-114d, outer electrodes 116b-116d, and the intervening portions 324b-424d of piezoelectric body 110. In the embodiment of FIG. 4A, the transducer elements are connected in series in an alternating field configuration relative to the direction of polarization of the piezoelectric material. To illustrate this conveniently, arrows 328 indicate the direction of polarization, and double arrows 330a-330d indicate the field direction relative to the direction of polarization. Plus (+) and minus (−) signs at the electrodes of the transducer elements indicate instantaneous voltage drop directions for a voltage having the polarity indicated at input terminals 310 and 312, by which transducer 300 is connected to a power supply (not shown). Thus, for the illustrated embodiment, terminals 310 and 312 are connected to terminals 114a and 114d, respectively, of transducer elements 118a and 118d. Terminals 116a and 116b of transducer elements 118a and 118b are connected together by a signal path 314, and the terminals 114b and 114c of transducer elements 118b and 118c are connected together by a signal path 318. Terminals 116c and 116d of transducer elements 118c and 118d are connected together by a signal path 316. As a consequence, the induced electric fields in adjacent transducer elements are in opposite (alternating) directions, and the mechanical vibrations generated by adjacent sectors are 180° out of phase relative to each other. FIG. 4B shows a schematic bottom plan view of transducer 300 and an exemplary wiring layout by which the electrical configuration of FIG. 4A may be achieved. In the figure, electrodes 114a-114d on the concave, bottom side of the transducer elements 118a-118d, respectively, are shown.

The embodiment illustrated in FIGS. 4A and 4B exhibits a circumferential focal pattern with one peak for each transducer element. In addition, since the impedance of N like circuit elements connected in series is related to N times the impedance of a single element, while the impedance of N such elements connected in parallel is related to 1/N times the impedance of a single element, the four-element series-connected transducer illustrated in FIG. 4 exhibits electrical impedance which can be 16 times that of conventional transducers having the same elements connected in parallel.

Figures 5A, 5B:
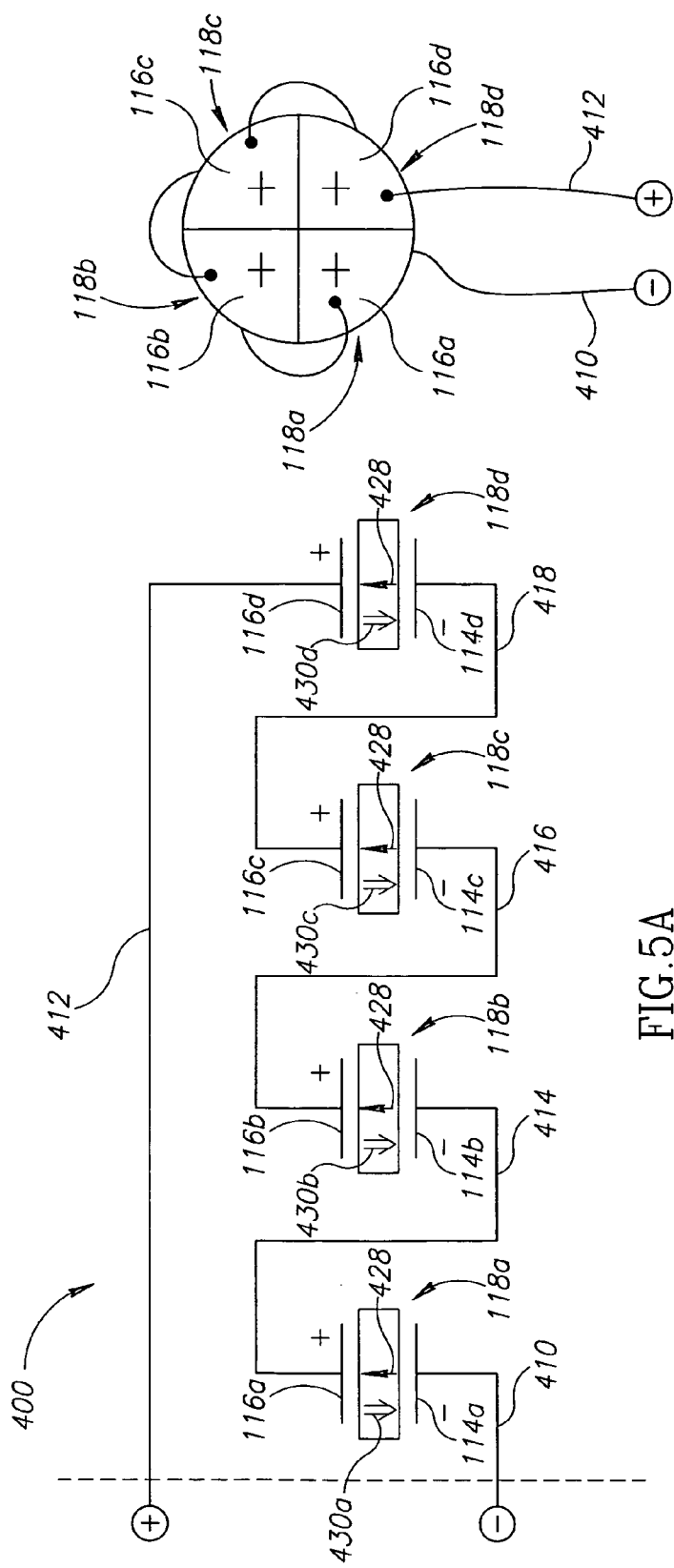
FIGS. 5A to 5B illustrate electrical schematic diagrams, according to some embodiments.

An additional embodiment is illustrated in FIGS. 5A and 5B. Here, a four-element transducer 400 is arranged with its elements 118a-118d connected in series in matched field configuration. Thus, input leads 410 and 412 are connected respectively to the "−" side terminal 114a of element 118a, and the "+" side terminal 116d of element 118d. Likewise, the "+" side terminal 116a of element 118a is connected to the "−" side terminal 114b of element 118b by signal path 414, the "+" side terminal 116b of element 118b is connected to the "−" side terminal 114c of element 118c by a signal path 416, and the "+" side terminal 116c of element 118c is connected to the "−" side terminal 114d of element 118d by a signal path 418. As a consequence, the electric fields (indicated by double arrows 430a-430d) are in the same direction relative to the polarization of the piezoelectric material (indicated by single arrows 428) in all of the transducer elements, and the mechanical vibrations generated by all the elements are in phase relative to each other. FIG. 5B is a schematic top plan view of transducer 400 which shows electrodes 116a-116d, and an exemplary wiring layout by which the electrical configuration of FIG. 5A may be achieved. The embodiment illustrated in FIGS. 5A and 5B exhibits an axial focal pattern, that is, having one peak along the transducer axis. In addition, like the embodiment of FIGS. 5A and 5B, the impedance can be 16 times that of prior art transducers in which the elements are connected in parallel. In some instances, it is desirable to be able to switch a transducer between the alternating field configuration of FIGS. 4A and 4B and the matched field configuration of FIGS. 4A and 4B. This can be achieved by connecting the input terminals (designated as 310 and 312 in FIGS. 4A and 4B and as 410 and 412 in FIGS. 5A and 5B) and the signal paths between the transducer elements through an appropriate switching circuit as illustrated schematically in FIG. 8.

Here, a four-element transducer such as transducer 300 illustrated in FIG. 4A (or transducer 400 illustrated in FIG. 5A) has its elements 118a-118d connected to a switching circuit 702. Terminals PS1 and PS2, by which a power supply (not shown) is connected to energize the transducer, are provided on switching circuit 702, and also a set of control terminals Cl-Cn. As will be understood by those skilled in the art, there are numerous suitable internal configurations for switching circuit 702, and details of such configurations are omitted in the interest of brevity.

Figure 8:
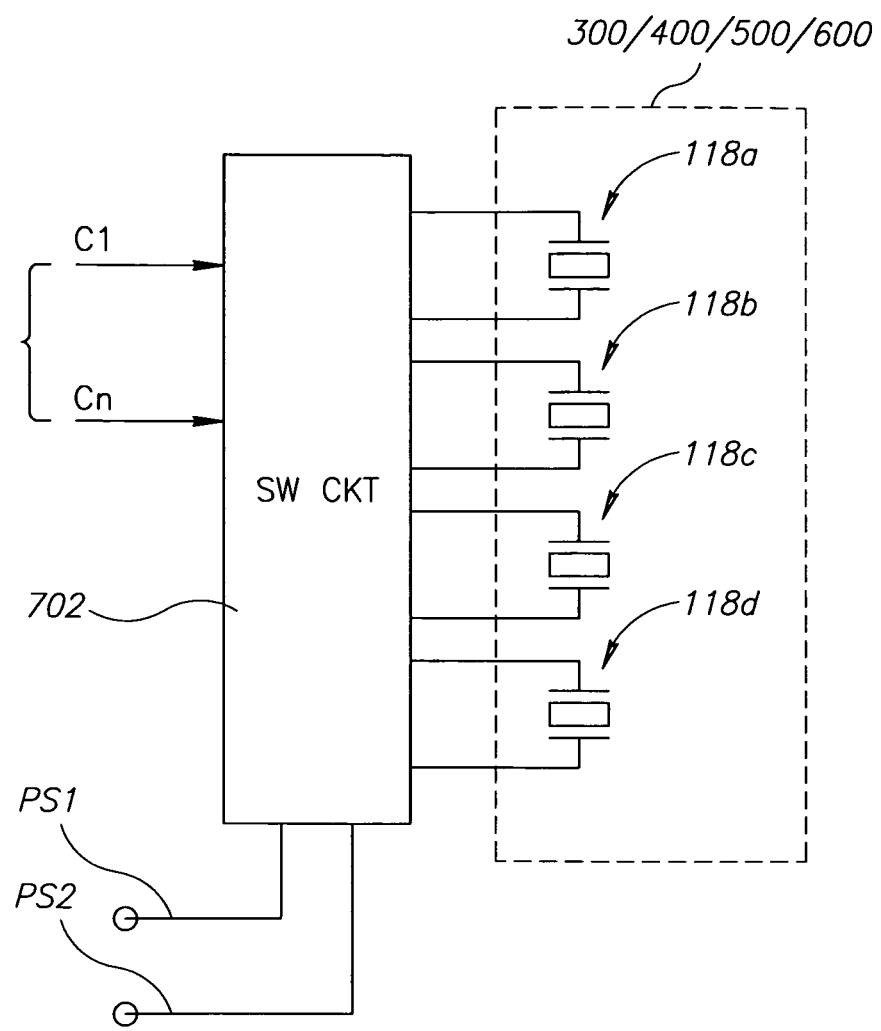
FIGS. 8 is a schematic diagram showing connection of a multi-element transducer to a switching circuit, according to some embodiments.

Using a switching circuit as illustrated in FIG. 8, it is possible to switch between series-connected alternating and matched field configurations as shown in FIGS. 4A and 5A to selectably obtain an axial or circumferential focal pattern. Using such a switching circuit with appropriate internal connections, it is also possible to obtain alternating and matched field configurations in which the transducer elements are connected in parallel. An alternating field configuration, with the transducer elements connected in parallel, is illustrated in FIGS. 6A and 6B.

Here, a four-element transducer 500, having the same piezoelectric transducer element configuration as illustrated in FIGS. 4A and 5A, is arranged so that a first power supply terminal 510 is connected to the "+" side terminals 116a and 116c of transducer elements 118a and 118c, and to the "−" side electrodes 114b and 114d of transducer elements 118b and 118d. A second power supply terminal 512 is connected to the "−" side terminals 114a and 114c of transducer elements 118a and 118c, and the "+" side terminals 116b and 116d of transducer elements 118b and 118d. As in the case of transducer 300 (see FIG. 4), the induced electric fields (indicated by double arrows 530a-530d) are in opposite directions relative to the polarization of the piezoelectric material in adjacent transducer elements (indicated by single arrows 528), and the mechanical vibrations generated by adjacent transducer elements are 180° out of phase relative to each other. FIG. 6B shows a top plan view of transducer 500, with electrodes 116a-116d visible, and an exemplary wiring layout by which the electrical configuration of FIG. 6A may be achieved.

Figures 6A, 6B:
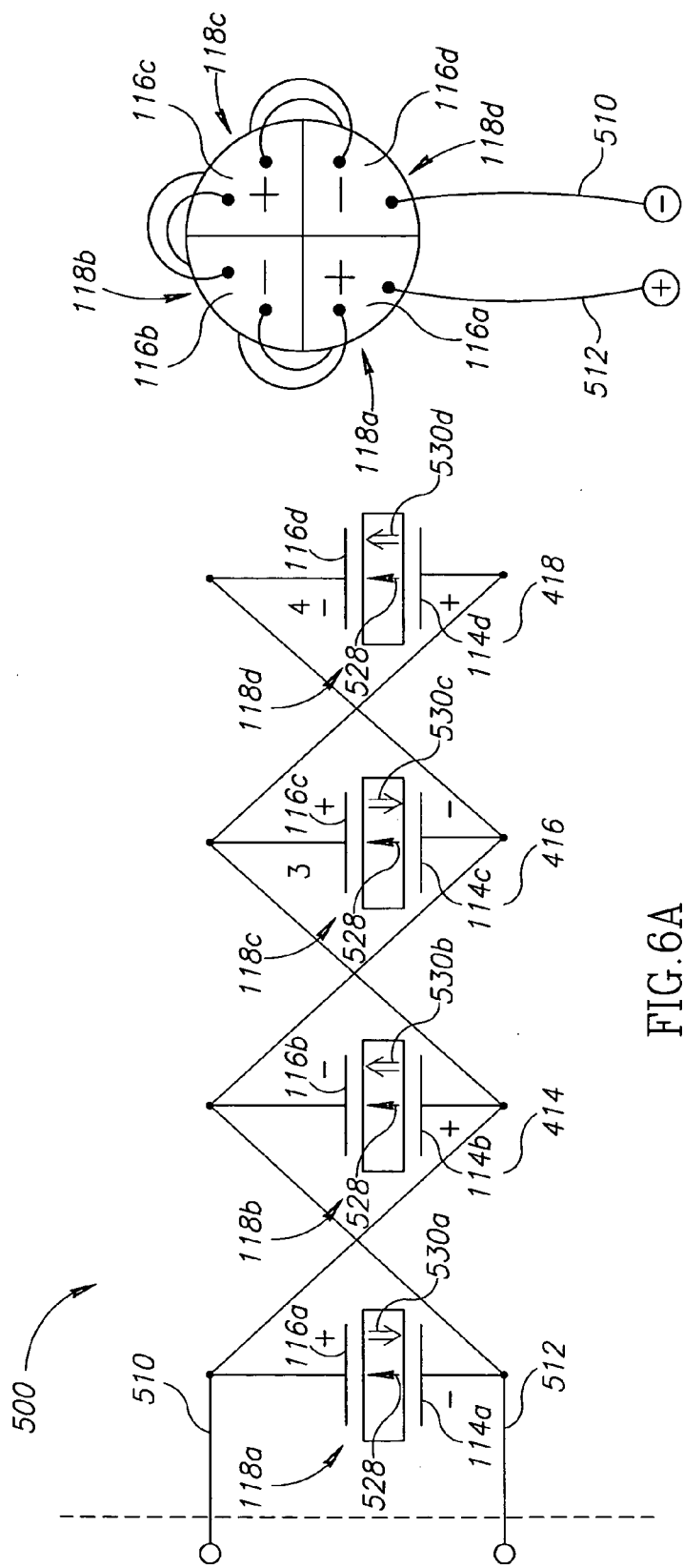
FIGS. 6A to 6B illustrate electrical schematic wiring layouts, according to some embodiments.

The arrangement illustrated in FIGS. 6A and 6B exhibits a circumferential focal pattern with one peak for each transducer segment. However, its electrical impedance is lower by a factor of about 16 as explained above, compared to that of the series connected configuration shown in FIGS. 4A and 4B. The configuration of FIGS. 6A and 6B can readily be provided for in the design of switching circuit 702, as will be apparent to those skilled in the art in light of the description herein.

A parallel-connected transducer having a matched-field configuration may also be provided for in the design of switching circuit 702. Such a transducer configuration is shown at 600 in FIGS. 7A and 7B. Here, power supply terminals 610 and 612 are respectively connected to the "+" and "−" side terminals 116a-116d and 114a-114d of all the transducer elements 118a-118d. As in the embodiment of FIG. 5, the electric fields (indicated by double arrows 630a-630d) are in the same direction relative to the polarization of the piezoelectric material (indicated by single arrows 628) in all of the transducer elements, and the mechanical vibrations generated by all the elements are in phase relative to each other. FIG. 7B shows a top plan view of transducer 600, with electrodes 116a-116d visible, and an exemplary wiring layout by which the electrical configuration of FIG. 7A may be achieved.

The configuration of FIGS. 7A and 7B is characterized by an axial focal pattern and electrical impedance at 1 MHz that is lower than that of the corresponding serially connected transducer of FIGS. 5A and 5B by a factor of 16.

From the foregoing description, it will readily be appreciated that desirable electrical impedance levels can be achieved by taking advantage of the polarization of piezoelectric ceramic material and by connecting a segmented transducer with the elements in series, either in an alternating polarization configuration or in a matched polarization configuration. By the use of a switching circuit of straightforward design, the same multi-element transducer construction can be used to provide both alternating and matched polarization configurations, and to provide these configurations with series-connected elements or parallel-connected elements, thereby achieving flexibility in selection of both focal patterns, and electrical impedance. While the transducers discussed above are all constructed of four elements, any other desired even numbers of elements are also possible. As will be appreciated, as the number of elements is increased, the relative increase in impedance for series-connected arrangements compared to parallel-connected arrangements will be larger.

In addition, according to further embodiments, it is also possible to obtain a multiple-element transducer having an alternating field configuration without the need for multiple isolated electrode pairs. To this aim, instead of being formed with a uniform direction of polarization, the piezoelectric body is formed with any desired number of alternating zones, such as, for example, four adjacent zones of alternating polarization. This may be done, for example, by applying a suitable electric polling field with the desired polarity to each zone. After the piezoelectric body has been polarized, inner and outer metallic coatings are applied, as previously described, but optionally, coatings are not scored to create separate electrode pairs. In that event, there is a single inner electrode and a single outer electrode. Thus, for a given voltage polarity applied to the transducer, the field direction does not reverse from zone to zone, but because the direction of polarization of the piezoelectric body alternates between zones, and a circumferential focal pattern is achieved. It should be noted that, for a configuration having single inner and outer electrodes, the transducer elements are connected in parallel, as in the arrangement shown, for example, in FIGS. 6A and 6B.

Figure 9A:
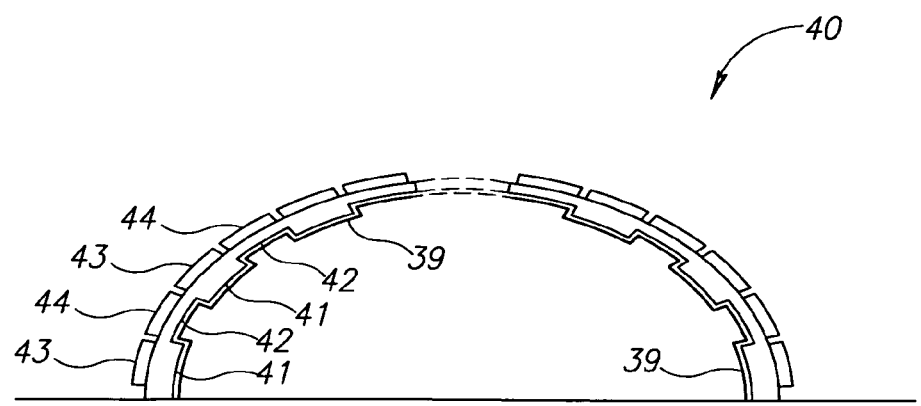
FIGS. 9A-9B schematically illustrates transducer heads constructed to operate at multiple frequencies by means of regions of different thickness, according to some embodiments.

Some applications of HIFU treatments require the use of ultrasound of different frequencies, or of combinations of frequencies, as outlined in applicants' U.S. Provisional Patent Application No. 61/064,581, entitled "Operation of Patterned Ultrasonic Transducers". There are a number of ways in which such an output can be generated from a transducer head constructed according to various embodiments of the present disclosure. Reference is now made to FIG. 9A, which illustrates schematically a preferred embodiment of a transducer head 40, according to the present disclosure, constructed to operate at multiple frequencies. The base piezoelectric transducer material is of similar shape to that of the embodiment shown in FIG. 1A, except that it is constructed with regions having different thicknesses. Thus in region 41, the material is thicker than in region 42. Using the exemplary data given for the embodiment of FIG. 1A, if the thinner regions 42 are made to be of the order of 1.7 mm thick, they will emit at approximately 1 MHz, while for a 8.4 mm thickness of the thicker regions 41, the frequency will be of the order of 200 kHz. The positions of the electrode elements can be arranged such that they generally overlap the positions of the different thickness regions, each of the thickness regions 41, 42, having their own individual exciting electrode elements 43, 44, such that it is possible to excite each frequency according to the electrode elements which are activated. The inner surface may have one or more electrodes, such as, for example electrode 39. Thus, when an electrode element 43 is activated, a 200 kHz beam is emitted from the section of piezoelectric material 41 below it, while activation of electrode elements 44 results in a 1 MHz beam. By activating both sets of electrode elements together, or by activating at least some of each of the electrode elements together, it also becomes possible to treat the target area with two frequencies simultaneously, which may be advantageous. The inner surface of the transducer is provided with common electrode 39. Additionally, it may be possible to excite heterodyne frequencies arising from beating of the two frequencies, if the ultrasound emitted from the two sets of electrode elements impinge together on the target zone. The embodiment of FIG. 9A shows only two different thickness regions, although it is to be understood that a larger number of different thicknesses can also be implemented, each thickness region vibrating at its own characteristic frequency.

Figure 9B:
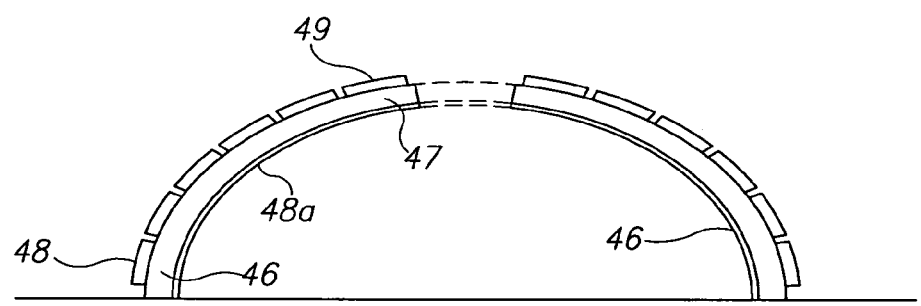

Although the embodiment of FIG. 9A shows sharp transition steps between the different thicknesses, it is to be understood that the transitions can also be gradual. Such an embodiment is shown in FIG. 9B where the thickness of the transducer material is gradually changed across the width of the transducer, being in the example of FIG. 9B, thicker 47 in the center of the transducer, and thinner 46 at the extremities. A range of frequencies can then be emitted by such a transducer. Thus, when electrode elements such as 49 are excited at the appropriate frequency, the emitted vibrational frequency is lower than, for instance, electrode elements such as 48. The inner surface may have one or more electrodes, such as, for example, electrode 48a.

Figure 10:
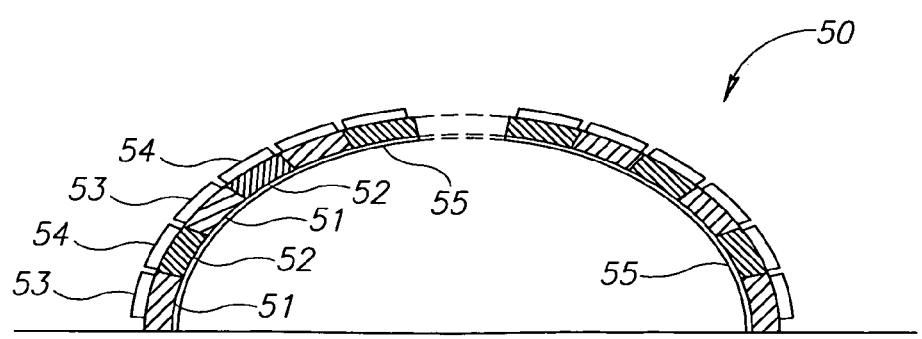
FIG. 10 shows schematically a single element transducer constructed to operate at multiple frequencies.

An alternative method of generating different frequencies is shown in FIG. 10, which shows schematically a single unitary element transducer 50 having regions of different material characteristics or constitution, such that they vibrate at different frequencies. The different regions can be of either different stoichometric composition, or of different doping levels, or of different densities, all as determined by the mixing and firing methods used for producing the ceramic, if the piezoelectric material is a ceramic. In the example shown in FIG. 10, two different types of regions are shown, one type being designated by the cross hatching 51, and the other by the longitudinal shading 52. Each region has its own characteristic electrode elements, 53, 54, located to excite just that region in juxtaposition to the electrode, such that application of the activating voltage to one or other of the electrode elements 53, 54, can result in different frequency ultrasonic beams being emitted. The inner surface may have one or more electrodes, such as, for example electrode 55. The embodiment of FIG. 10 shows only two types of transducer regions, although it is to be understood that a larger number of different types of regions can also be implemented, each type vibrating at its own characteristic frequency.

Figure 11A:
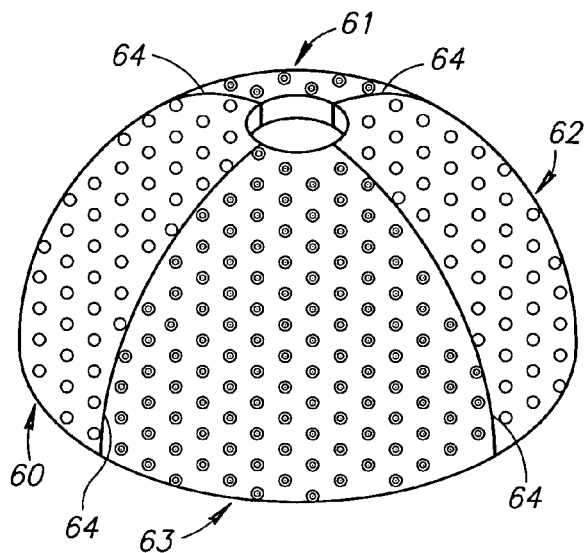
FIGS. 11A to 11C schematically illustrate possible arrangements of segmented electrode transducer elements with such a small number of segments.
Figure 11B:
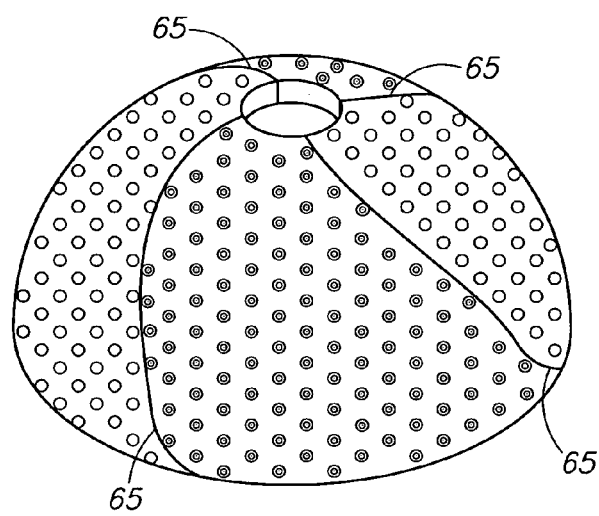
Figure 11C:
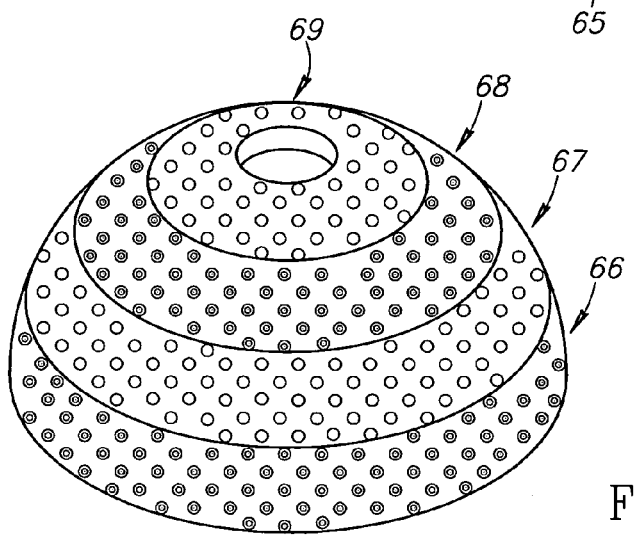

In the above described transducer heads, the electrode elements have been comparatively small, such that the transducer is made up of a large number of separate segmented transducers by virtue of the electrode elements. According to different embodiments, this number can run even up to over one hundred transducer segments, such a division being difficult to execute without the segmented electrode technology of the present disclosure. Cutting and sticking together such a large number of small elements is a difficult task to perform reliably and cost-effectively. However, it is to be understood that the present disclosure also provides advantages for embodiments where there are only a small number of segments in the transducer, starting with only two segments. As previously stated, the degrading effect of high power ultrasound on any adhesive joint may affect such assembled multiple segment transducers. Therefore, there are advantages even in a two-segment transducer using a single ceramic base transducer, and electrode elements constructed and operative according to the methods of the present disclosure. Reference is now made to FIGS. 11A to 11C, which illustrate schematically some additional possible arrangements of segmented transducer elements with such -a small number of segments. FIG. 11A illustrates in plan schematic view, a four-segment transducer constructed of a single piece of piezoelectric material with four separate electrode elements 60-63, coated thereon, each electrode element being separately excitable by means of its own applied voltage. Inter-electrode element boundary lines 64 separate electrode elements 60-63. The four segments could have different thicknesses, or different properties, as described in the embodiments of FIGS. 9 and 10, such that each segment vibrates at a different frequency. FIG. 11B shows a transducer with a quadruple electrode element pattern, the inter-electrode element boundary lines having a curved "S" shape 65. Use of such an embodiment may possibly have some specific effects on the tissue, and use of the segmented electrode technique of the present disclosure considerably simplifies the task of manufacture of such a transducer. FIG. 11C shows another embodiment of a transducer with concentric electrode regions 66, 67, 68, applied to a single ceramic transducer element. Such an embodiment is useful for generating different phased emissions. It is to be understood that FIGS. 11A to 11C are only some of the possible shapes which can be constructed using the electrode elements of the present disclosure, and that this aspect of the disclosure is not meant to be limited to what is shown in exemplary embodiments of FIGS. 11A to 11C.

Alternatively, some of the segments could themselves have a pattern of electrode elements, such that the transducer head acts as a combination of large segment transducers, and an array of small segmented transducers.

Figures 12A, 12B, 12C:
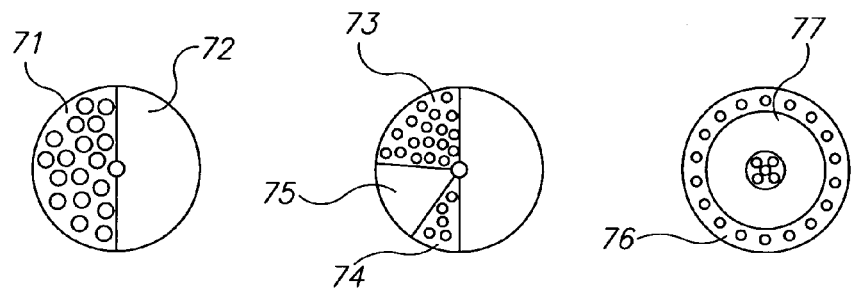
FIGS. 12A to 12C schematically illustrate additional possible arrangements of arrays of separate transducer elements, both symmetric and non-symmetric.

Reference is now made to FIGS. 12A to 12C, which illustrate schematically some additional possible arrangements of arrays of separate transducer elements, any of which may itself be operative as a multi-segmented transducer by virtue of an assembly of electrode elements on its surface, such that the transducer head acts as a combination of large segment transducers, and an array of small segmented transducers. The embodiment of FIG. 3F above shows one example of a transducer head made up of two separate unitary multi-segmented transducers. FIG. 12A shows a spherical transducer head, having two separate sectors, one of which is a single piece, single segment transducer 71, and another sector 72 having electrode elements over their surface. FIG. 12B shows an exemplary embodiment in plan view, in which there is a single piece array 73 covering a quarter of the transducer head, another multi-electrode element, single piece array 74 covering one eighth of the transducer head, and a further single piece, single electrode transducer 75 covering another eighth of the transducer head. FIG. 12C shows a cap with annular sections, similar to that shown in FIG. 11C, in which one section 76 is made up of a number of segmented annular sections, electrode transducers, some of which are single piece, multi-electrode element transducers with a large number of segments thereon, and other sections, such as section 77, being single piece, single transducers. Other combinations and arrangements are also possible, as will be evident to one of skill in the art.

Figure 13:
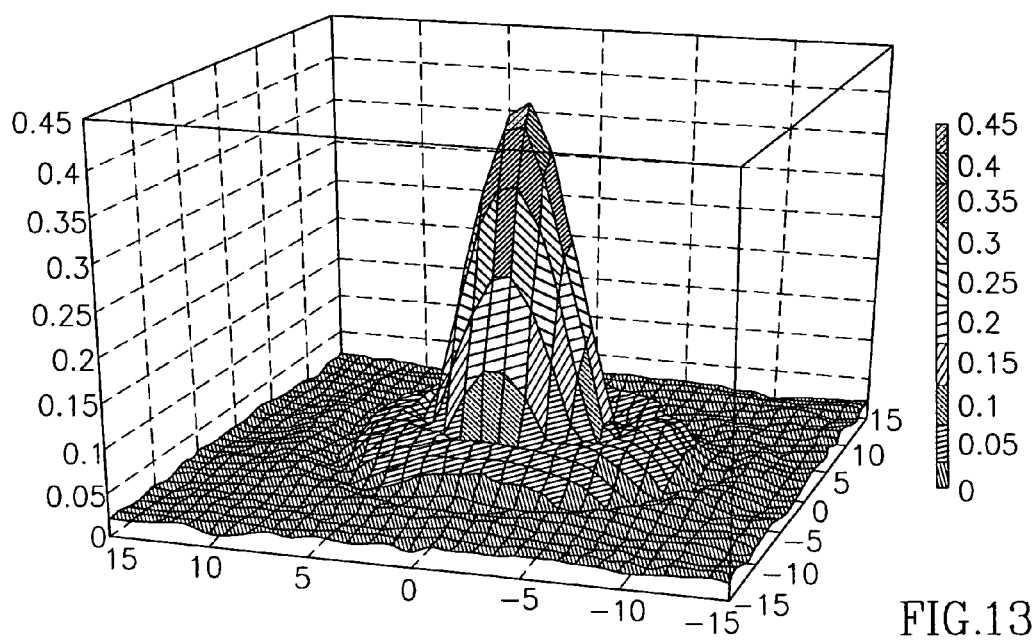
FIG. 13 illustrates hydrophone measurement of Acoustic field distribution in the focal plane of a transducer.
Figure 14:
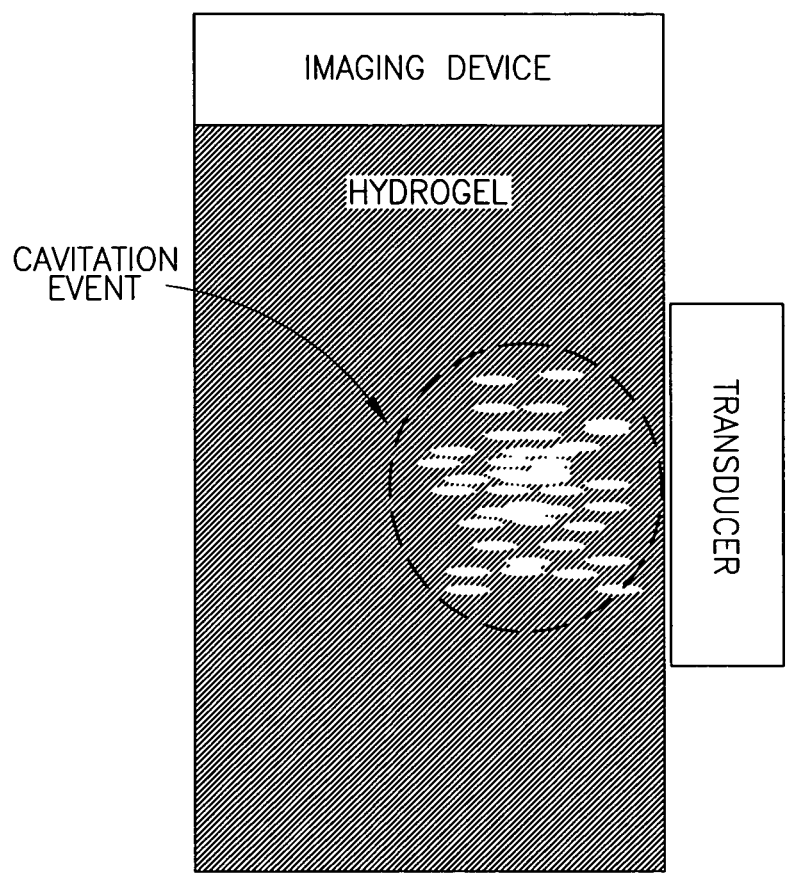
FIG. 14 illustrates an ultrasound image showing a cavitation event produced by a transducer in hydrogel.

According to some embodiments, and further to what is mentioned above, a transducer may be operative such that by selection and/or use of appropriate parameters, a selective formation of an effect, such as, for example, cavitation in a target tissue, may be achieved. For example, by selecting appropriate parameters, forming of cavitation in/on/at an adipose and/or cellulite tissue may be achieved, while adjoining and/or near and/or surrounding tissues (such as blood, muscle, nerve, connective or other tissues) may not be affected. Therefore, a transducer, with one or more transducing elements, as described above, may be constructed and operated with such parameters that maximal selectivity of its effect is achieved. For example, a transducer, comprising one or more transducing elements (zones), as described above may operate with the following exemplary parameters listed below to obtain selective effect on adipose/cellulite tissues and not on neighboring tissues. For simplicity, the parameters of a transducer with one transducing element (zone) are described below in the section Aspects of operation of ultrasonic transducer (Table 2). However, it will be evident to one of skill in the art that two or more transducing zones may be similarly operative, according to various embodiments of this disclosure. For example, for one transducing zone operating at an operating frequency in the range of about 0.19 to 0.21 MHz at a pulse operating mode, with a pulse duration in the range of, about 1.8 to 2.2 milliseconds (ms), with a pulse repetition period in the range of 34 to 46 ms, with exposure time of about 2.85 to 3.15 seconds per node, the following measurements are obtained: $I_{SPTA}$ of, about 16.0 to 20 W/cm$^2$; $I_{SPPA}$ of about 320 to 400 W/cm$^2$; Pr, in the focus, of about 3.5 to 4.5 (MPa), MI (MPa/(MHz)½) in the focus, of about 8 to 10 (MPa/(MHz)$^{1/2}$); Focus depth of about 12 to 16 mm; Focal Area diameter (in the focal plane) of about, 5 to 7 mm. The results show that the transducer (transducing zone) produces focused ultrasound with the maximum pressure value at the depth of 14 mm. The ratio of the acoustic pressure in the focus to the maximal pressure on the surface (skin) is in the range 3.5-4.0, which further ensures safety of the treatment. Results of testing the effects produced by the transducer element operative with the listed parameters are further detailed in Aspects 1 and 2 (FIGS. 13 and 14, respectively).

Comparing the results thus obtained from a transducing element operating with the parameters essentially as listed above, with those listed in Table 2, demonstrate the following points: 1. Although the pressure values in the focus are in the range of the diagnostic ultrasound, the $I_{SPTA}$ values are higher. In addition, calculated MI value (which characterizes the likelihood of mechanical damage) is averaged at about 9.0, which is significantly above the maximal allowed value 1.9 for diagnostic equipment and, as mentioned above, is in the range of the cavitation threshold in tissues. This means that the transducer element is selectively adapted to mechanically destruct fat cells. 2. The calculated $P_r$ and $I_{SPTA}$ values are much lower than those for HIFU applications listed in Table 1 (which include thermal, histotripsy and haemostasis procedures). A pulsed operation mode (with a duty cycle of about 5%), a comparatively low Pr and ISPTA values, and short exposure time per node practically exclude any noticeable heating that may be caused by the transducer. As detailed in Aspects 3 and 4 (FIG. 15 and 16, respectively), calculations of the spatial temperature rise distribution performed using the Pennes bio-heat equation (1) show that it does not exceed 0.5° C. in the focus area.

In view of the results obtained from the operating parameters presented above, the transducer element is not operative under the "classical" definition of HIFU. Rather, the transducer is operative in the Mid Intensity focused ultrasound (MIFU) and/or the low intensity focused ultrasound (LIFU). In spite of this definition, the treatment rendered by use should have the same cumulative effects as those of conventional HIFU, yet without the above-delineated disadvantages of conventional HIFU treatment.

Figure 17:
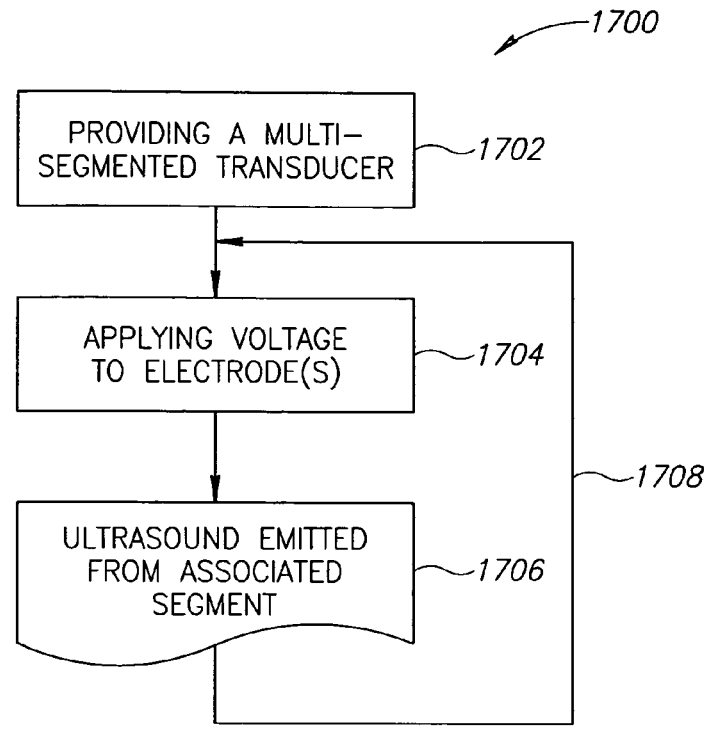
FIG. 17 illustrates a flow chart of a method for generating focused ultrasound energy.

Reference is now made to FIG. 17, which shows a flow chart 1700 illustrating a method for generating focused ultrasound energy for lysing of adipose tissues, according to an embodiment. In a block 1702, a multi-segmented transducer (also referred to as a "transducer array") is provided and positioned at a desired location. In a body contouring position, the transducer may be positioned substantially over a portion of a patient's body, above an approximate area of treatment.

In a block 1704, voltage is applied to at least one electrode and/or electrode element of the transducer. A plurality of electrode elements may be associated with a plurality of distinct segments of the transducer. Voltage may therefore be applied simultaneously and/or sequentially to one or more electrode elements, where at least some of the electrode elements may be associated with different segments.

In a block 1706, the applied voltage excites vibrations in one or more segments of the transducer, where each segment may be associated with one or more of the electrode elements. The vibrations induce emitting of ultrasonic waves from the piezoelectric material forming the transducer.

The application of voltage in block 1704, followed by the emitting of ultrasound in block 1706, may be repeated 1708 a desired number of times.

In an embodiment, a multi-segmented transducer is used in a body contouring procedure—a procedure wherein adipose tissues are destroyed for reshaping and essentially enhancing the appearance of a human body.

Figure 18:
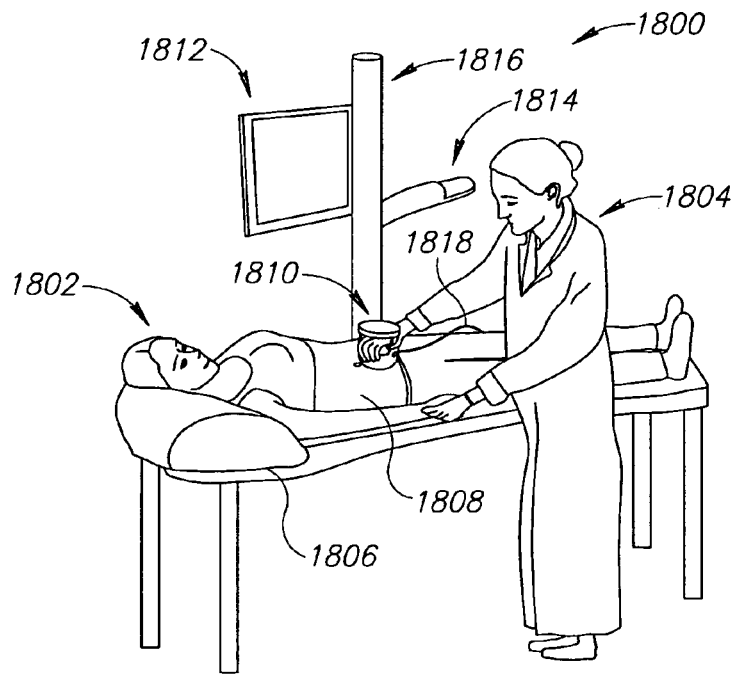
FIG. 18. illustrates a body contouring treatment of a patient.

Reference is now made to FIG. 18, which shows an exemplary treatment 1800 of a patient 1802 by a caregiver 1804. Caregiver 1804 may be, for example, a physician, a nurse and/or any other person legally and/or physically competent to perform a body contouring procedure involving non-invasive adipose tissue destruction. Patient 1802 optionally lies on a bed 1806 throughout treatment 1800.

Caregiver 1804 may hold a transducer unit 1810 against an area of patient's 1802 body where destruction of adipose tissue is desired. For example, transducer unit 1810 may be held against the patient's 1802 abdomen 1808. Transducer unit 1810 may comprise one or more multi-segmented transducers. Transducer unit 1810 may be connected by at least one wire 1818 to a controller (not shown) and/or to a power source (not shown).

Optionally, a user interface is displayed on a monitor 1812, which may be functionally affixed to a rack, such as pillar 1816. A transducer unit 1810 storage ledge 1814 may be provided on pillar 1816 or elsewhere.

Body contouring may be performed by emitting one or more ultrasonic pulses from transducer unit 1810 while it is held against a certain area of the patient's 1802 body. Then, transducer unit 1810 is optionally re-positioned above one or more additional areas and the emitting is repeated. Each position of transducer unit 1810 may be referred to as a "node". A single body contouring treatment may include treating a plurality of nodes.

Aspects of Operation of Ultrasonic Transducer

Listed in Table 2 are operating parameters of a transducer, the operating aspects of which are discussed below.

TABLE 2

| Operating Parameters | Value |
|---|---|
| Operating Frequency (MHz) | 0.2 ± 0.03 |
| Operating Modes | Pulsed (tone bursts) |
| Pulse Duration (ms) | 2.0 ± 15% |
| Pulse Repetition Period (ms) | 40 ± 15% |
| Exposure time per node (s) | 3.0 ± 5% |
| ISPTA (W/cm$^2$) | 18.0 ± 10% |
| ISPPA (W/cm$^2$) | 360.0 ± 10% |
| $P_r$ (MPa), in the focus | 4.0 ± 0.5 |
| M1 (MPa/(MHz)$^{1/2}$), in the focus | 9.0 ± 1.0 |
| Focus depth (mm) | 14.0 ± 2.0 |
| Focal Area diameter (in the focal plane), mm | 6.0 ± 1.0 |

Aspect 1—Acoustic field distribution in the focal plane of a transducer, measured in water with a hydrophone.

Shown in FIG. 13 is the acoustic field distribution in the focal plane of the transducer, measured in water with a hydrophone. The results show the distribution of the peak pressure (in units of MPa) in the focal plane of the transducer.

Aspect 2—A cavitation effect produced by the transducer in hydrogel and visualized by an imaging device (ultrasonic imager).

Shown in FIG. 14, a cavitation effect produced by the transducer in hydrogel and visualized by an ultrasound imager. The cavitation effect is demonstrated by white ellipses.

Aspect 3—Temperature variations with time in the focus.

Figure 15:
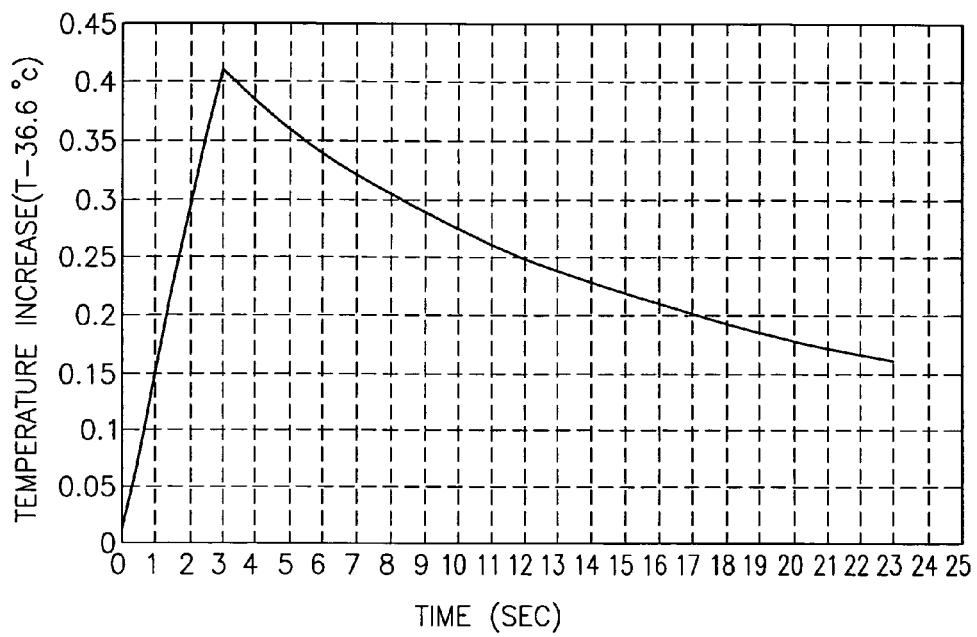
FIG. 15 illustrates a graph of the temperature variations with time in the focus.

Shown in FIG. 15, a graph illustrating temperature variation (in degrees Celsius) with time (Seconds) in the focus of the ultrasound.

Aspect 4—Radial temperature increase distribution in the focal plane.

Figure 16:
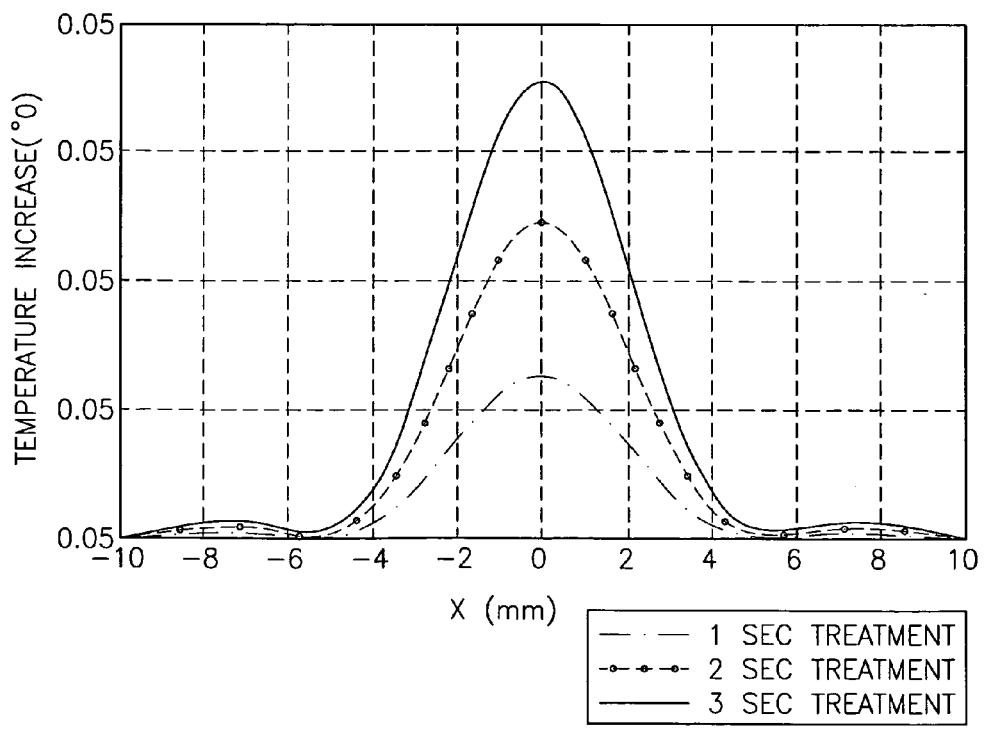
FIG. 16 illustrates a graph of the radial temperature increase distribution in the focal plane.

Shown in FIG. 16, a graph illustrating the distribution (measured in mm) of radial temperature increase (in degrees Celsius) after 1 second, 2 second and 3 second treatments, in the focal plane.

It is appreciated by persons skilled in the art that the present disclosure is not limited by what has been particularly shown and described hereinabove. Rather the scope of the present disclosure includes both combinations and sub-combinations of various features described hereinabove, as well as variations and modifications thereto, which would occur to a person of skill in the art upon reading the above description and which are not in the prior art.

What we claim is:

1. A device for lysing adipose tissue in a target area inside a body, the device comprising: a power source configured for energizing one or more of a plurality of individual transducer segments of a transducer, wherein the transducer is made of a spherical ceramic material wherein said transducer comprises a single unitary piece of ceramic and wherein the thickness of the transducer material is gradually changed across the width of the transducer; and the energized one or more of the plurality of individual transducer segments being configured for transmitting focused ultrasound towards a focal region having its major axis along the direction of the wave propagation, the focused ultrasound having a power density at the target area which is higher than a cavitation threshold.

2. The device according to claim 1, wherein the single unitary piece of ceramic between said first internal concave surface and second opposite external convex surfaces comprises at least two segment that are configured differently for at least the material of which they are constructed; and wherein said at least two segments have their own individual exciting electrode elements.

* * * * *